US011655506B2

(12) United States Patent
Plaas et al.

(10) Patent No.: US 11,655,506 B2
(45) Date of Patent: May 23, 2023

(54) THERAPEUTIC TARGET FOR MUSCULOSKELETAL INFLAMMATION

(71) Applicants: Rush University Medical Center, Chicago, IL (US); The Board of Trustees of the University of Illinois, Urbana, IL (US)

(72) Inventors: Anna Plaas, Chicago, IL (US); Vincent Wang, Naperville, IL (US); John Sandy, Chicago, IL (US); Rebecca Bell, New York, NY (US); Jorge Galante, Sanibel, FL (US); Katie J. Trella, Chicago, IL (US)

(73) Assignees: Rush University Medical Center, Chicago, IL (US); The Board of Trustees of the University of Illinois, Urbana, IL (US)

( * ) Notice: Subject to any disclaimer, the term of this patent is extended or adjusted under 35 U.S.C. 154(b) by 767 days.

(21) Appl. No.: 15/111,395

(22) PCT Filed: Jan. 14, 2015

(86) PCT No.: PCT/US2015/011380
§ 371 (c)(1),
(2) Date: Jul. 13, 2016

(87) PCT Pub. No.: WO2015/108958
PCT Pub. Date: Jul. 23, 2015

(65) Prior Publication Data
US 2016/0333410 A1 Nov. 17, 2016

Related U.S. Application Data

(60) Provisional application No. 61/927,070, filed on Jan. 14, 2014.

(51) Int. Cl.
*C12Q 1/6883* (2018.01)
*G01N 33/68* (2006.01)
*A61K 38/18* (2006.01)
*A61K 38/43* (2006.01)

(52) U.S. Cl.
CPC ........ *C12Q 1/6883* (2013.01); *A61K 38/1841* (2013.01); *A61K 38/43* (2013.01); *G01N 33/6887* (2013.01); *C12Q 2600/158* (2013.01); *G01N 2800/10* (2013.01); *G01N 2800/52* (2013.01)

(58) Field of Classification Search
CPC .......... G01N 33/6887; G01N 2800/10; G01N 2800/52; A61K 38/1841; A61K 38/43; C12Q 1/6883; C12Q 2600/158
See application file for complete search history.

(56) References Cited

U.S. PATENT DOCUMENTS

| | | | | |
|---|---|---|---|---|
| 2004/0229805 A1* | 11/2004 | Ardies | ................. | C12Q 1/6886 514/44 R |
| 2007/0299517 A1* | 12/2007 | Davisson | ............ | A61L 27/3604 623/11.11 |
| 2011/0218116 A1* | 9/2011 | Cook | .................. | C12Q 1/6883 506/9 |
| 2013/0137761 A1* | 5/2013 | Prehm | ................. | C07D 311/32 514/456 |

OTHER PUBLICATIONS

Bell et al. (2013) J. Biomechanics 46(3): 498-505. Available online Nov. 13, 2012. (Year: 2013).*
Voleti et al. (2012) Ann. Rev. Biomed. Eng. 14:47-71. (Year: 2012).*
Huang et al. (2008) J. Intl Med Res 36(6): 1149-1160 (Year: 2008).*
Verma et al. (2011) J Cell Biochem 112: 3507-3514 (Year: 2011).*
Baar et al. Arthritis & Rheumatism vol. 42(7). pp. 1361-1369 (Year: 1999).*
Arya et al.; "Tendinopathy alters mechanical and material properties of the Achilles tendon"; Journal of Applied Physiology, vol. 108; Mar. 1, 2010; 670-675.
Bell et al.; "ADAMTS5 is required for biomechanically-stimulated healing of murine tendinopathy"; Journal of Orthopaedic Research, vol. 31; Oct. 1, 2013; pp. 1540-1548.
Bell et al.; "Controlled Treadmill Exercise Eliminates Chondroid Deposits and Restores Tensile Properties in a New Murine Tendinopathy Model"; Journal of Biomechanics, vol. 46; Nov. 13, 2012; pp. 498-505.
Burssens et al.; "Arguments for an increasing differentiation towards fibrocartilaginous components in midportion Achilles tendinopathy"; Knee Surgery, Sports Traumatology, Arthroscopy, vol. 21; Jun. 1, 2013; pp. 1459-1467.
Chang et al.; "Studies in flexor tendon wound healing: neutralizing antibody to TGF-β1 increases postoperative range of motion"; Plastic and Reconstructive Surgery, vol. 105, Jan. 2000; pp. 148-155.
Chen et al.; "Histone Deacetylase Inhibitors: The Epigenetic Therapeutics That Repress Hypoxia-Inducible Factors"; Journal of Biomedicine and Biotechnology, vol. 2011, Article ID197946; Dec. 5, 2010; 14 pages.

(Continued)

*Primary Examiner* — Blaine Lankford
(74) *Attorney, Agent, or Firm* — Barnes & Thornburg LLP

(57) ABSTRACT

A method for monitoring a treatment of a subject having a musculoskeletal disorder is provided. The method includes measuring a first expression level of at least two biomarkers at a treatment site prior to the treatment and measuring a second expression level of the at least two biomarkers at the treatment site after the treatment begins. The method further includes comparing the first expression level of the at least two biomarkers prior to the treatment to the second expression level of the at least two biomarkers post treatment and continuing the treatment, altering the treatment or stopping the treatment based on the comparison. A method of treating a musculoskeletal disorder in a subject is also provided. The method includes removing a aggrecan-hyaluronan matrix from a treatment site in the subject.

5 Claims, 13 Drawing Sheets

(56) References Cited

OTHER PUBLICATIONS

Corps et al.; "Increased expression of aggrecan and biglycan mRNA in Achilles tendinopathy"; Rheumatology, vol. 45; Mar. 1, 2006; pp. 291-294.
Corps et al.; "Changes in matrix protein biochemistry and the expression of mRNA encoding matrix proteins and metalloproteinases in posterior tibialis tendinopathy"; Annals of the Rheumatic Diseases, vol. 71; May 1, 2012; pp. 746-752.
Estellar; "Molecular Origins of Cancer: Epigenetics in Cancer"; The New England Journal of Medicine, vol. 358, No. 11; Mar. 13, 2008; pp. 1148-1159.
Grabiec et al.; "Function of Histone Deacetylase Inhibitors in Inflammation" Critical Reviews in Immunology, vol. 31; 2011; pp. 233-263.
Jones et al.; "Expression Profiling of Metalloproteinases and Tissue Inhibitors of Metalloproteinases in Normal and Degenerate Human Achilles Tendon"; Arthritis & Rheumatism, vol. 54, No. 3; Mar. 2006; pp. 832-842.
Kannus et al.; "Histopathological changes preceding spontaneous rupture of a tendon. A controlled study of 891 patients"; Journal of Bone and Joint Surgery, vol. 73-A; Dec. 1991; pp. 1507-1525.
Legard et al.; "EGR1 and EGR2 Involvement in Vertebrate Tendon Differentiation"; Journal of Biological Chemistry, vol. 286; Feb. 18, 2011; pp. 5855-5867.
Li et al.; "Knockout of ADAMTS5 does not eliminate cartilage aggrecanase activity but abrogates joint fibrosis and promotes cartilage aggrecan deposition in murine osteoarthritis models"; Journal of Orthopaedic Research, vol. 29; Apr. 2011; pp. 516-522.
Li et al.; "Hyaluronan injection in murine osteoarthritis prevents TGFbeta 1-induced synovial neovascularization and fibrosis and maintains articular cartilage integrity by a CD44-dependent mechanism"; Arthritis Research & Therapy, vol. 14; Jun. 21, 2012; R151; 16 pages.
Liu et al.; "Crucial transcription factors in tendon development and differentiation their potential for tendon regeneration"; Cell and Tissue Research, vol. 356; May 1, 2014; pp. 287-298.
Luu et al.; "Integrin-substrate interactions underlying shear-induced inhibition of the inflammatory response of endothelial cells"; Thrombosis and Haemostasis, vol. 109; Feb. 1, 2013; pp. 298-308.
Maeda et al.; "Conversion of mechanical force into TGF-beta-mediated biochemical signals"; Current Biology, vol. 21; Jun. 7, 2011; pp. 933-941.
Malfait et al.; "ADAMTS-5 deficient mice do not develop mechanical allodynia associated with osteoarthritis following medical meniscal destabilization" Osteoarthritis and Cartilage, vol. 18; Apr. 30, 2010; pp. 572-580.
Millar et al.; "Hypoxia: a critical regulator of early human tendinopathy"; Annals of the Rheumatic Diseases, vol. 71; Feb. 1, 2012; pp. 302-310.
De Mos et al.; "In vitro model to study chondrogenic differentiation in tendinopathy"; The American Journal of Sports Medicine, vol. 37; Mar. 11, 2009; Abstract.
Mousavizadeh et al.; "Cyclic Strain Alters the Expressoin and Release of Angiogenic Factors by Human Tendon Cells"; Pios One, vol. 9, Issue 5; May 13, 2014; e97356; 8 pages.
Nganvongpanit et al.; "Evaluation of serum chondroitin sulfate and hyaluronan: biomarkers for osteoarthritis in canine hip dysplasia"; Journal of Veterinary Science, vol. 9, No. 3; Sep. 1, 2008; pp. 317-325.
Pingel et al.; "Local biochemical and morphological differences in human Achilles tendinopathy: a case control study"; BMC Musculoskeletal Disorders, vol. Apr. 5, 13, 2012; 13 pages.
Plaas et al.; "Aggrecanolysis in human osteoarthritis: confocal localization and biochemical characterization of ADAMTS5-hyaluronan complexes in articular cartilages"; Osteoarthritis and Cartilage, vol. 15; Jul. 31, 2007; pp. 719-734.
Plaas et al.; "Intraarticular injection of hyaluronan prevents cartilage erosion, periarticular fibrosis and mechanical allodynia and normalizes stance time in murine knee osteoarthritis"; Arthritis Research & Therapy, vol. 13; Mar. 20, 2011; R46; 14 pages.
Plaas et al.; "The relationship between fibrogenic TGFbetal signaling in the joint and cartilage degradation in post-injury osteoarthritis"; Osteoarthritis Cartilage, vol. 19; Sep. 30, 2011; pp. 1081-1090.
Plaas et al.; "Biochemical identification and immunolocalizaton of aggrecan, ADAMTS5 and inter-alpha-trypsin-inhibitor in equine degenerative suspensory Tigament desmitis"; Journal of Orthopaedic Research, vol. 29; Jun. 1, 2011; pp. 900-906.
Robinson et al.; "Epigenetics within the Matrix: A neo-regulator of fibrotic disease"; Epigenetics, vol. 7; Sep. 2012; pp. 987-993.
Samiric et al.; "Changes in the composition of the extracellular matrix in patellar tendinopathy"; Matrix Biology, vol. 28; May 31, 2009; pp. 230-236.
Scaffidi et al.; "$\alpha_v\beta_3$ integrin interacts with the transforming growth factor $\beta$ (TGF$\beta$) type II receptor to potentiate the proliferative effects of TGF$\beta$1 in living human lung fibroblasts"; The Journal of Biological Chemistry, vol. 279; Sep. 3, 2004; pp. 37726-37733.
Semenza; "Regulation of Mammalian $0_2$ Homeostasis by Hypoxia-Inducible Factor 1"; Annual Review of Cell and Developmental Biology; Nov. 1999 pp. 551-578.
Shoshani et al.; "Cell Isolation Induces Fate Changes of Bone Marrow Mesenchymal Cells Leading to Loss or Alternatively to Acquisition of New Differentiation Potentials" Stem Cell, vol. 32; Aug. 1, 2014; pp. 2008-2020.
Silbernagel et al.; "The majority of patients with Achilles tendinopathy recover fully when treated with exercise alone: a 5-year follow-up"; The American Journal of Sports Medicine, vol. 39; Mar. 2011; pp. 607-613.
Velasco et al.; "AdamtsS deletion blocks murine dermal repair through CD44-mediated aggrecan accumulation and modulation of transforming growth factor $\beta$1 (TGF$\beta$1) signaling"; The Journal of Biological Chemistry, vol. 286; Jul. 22, 2011; pp. 26016-26027.
De Vlaming et al.; "Atrioventricular valve development: New perspectives on an old theme"; Differentiation, vol. 84; Jul. 2012; pp. 103-116.
Wang et al.; "Variability in tendon and knee joint biomechanics among inbred mouse strains"; Journal of Orthopaedic Research, vol. 24; Jun. 2006; pp. 1200-1207.
Wang et al.; "Murine tendon function is adversely affected by aggrecan accumulation due to the knockout of ADAMTS5"; Journal of Orthopaedic Research, vol. 30; Apr. 2012; pp. 620-626.
International Search Report completed Mar. 19, 2015 for International Application No. PCT/US2015/011380.

* cited by examiner

THERAPEUTIC TARGET FOR MUSCULOSKELETAL INFLAMMATION

RELATED APPLICATIONS

This application claims the benefit under 35 U.S.C. § 371 of International Application No. PCT/US2015/011380, filed Jan. 14, 2015, which claims the benefit of U.S. Provisional Application No. 61/927,070, filed Jan. 14, 2014, which are incorporated by reference herein in their entirety.

FEDERALLY SPONSORED RESEARCH OR DEVELOPMENT

This invention was made with government support under federal grant numbers RO1-AR057066 and RO1-AR063144-01A1 awarded by National Institutes of Health. The government has certain rights in the invention.

TECHNICAL FIELD

The present invention relates to methods of monitoring treatments and methods of treating musculoskeletal disorders, and in particular the method of treating musculoskeletal disorders relates to reducing an amount of an aggrecan-hyaluronan matrix from a treatment site.

BACKGROUND

Human tendinopathies (e.g. Achilles, rotator cuff, epicondylitits) have been characterized histologically by the variable presence of features such as increased cellularity, collagen disorganization, mucoid degeneration, lipid accumulation and calcific deposits. In contrast to the fibrocartilage that forms in adaptation to normal mechanical compression, mucoid deposits appear to be a pathologic response to an abnormal biochemical and/or biomechanical environment within the tendon body. Data on the mechanisms underlying generation of mucoid deposits and its likely pathogenic effects in tendinopathy have not been forthcoming.

Effective treatment options for human tendinopathies are limited currently. What is needed is a method of monitoring treatments to more effectively provide treatment for musculoskeletal disorders. Additional methods of treatment for musculoskeletal disorders are also needed.

BRIEF SUMMARY

A method for monitoring a treatment of a subject having a musculoskeletal disorder is provided. The method includes measuring a first expression level of at least two biomarkers at a treatment site prior to the treatment and measuring a second expression level of the at least two biomarkers at the treatment site after the treatment begins. The method further includes comparing the first expression level of the at least two biomarkers prior to the treatment to the second expression level of the at least two biomarkers post treatment, and continuing the treatment, altering the treatment or stopping the treatment based on the comparison.

A method of treating a musculoskeletal disorder in a subject is provided. The method includes removing a aggrecan-hyaluronan matrix from a treatment site in the subject.

values and the mean (with standard deviation plotted as error bars) of the normalized values are present.

Figure 11:
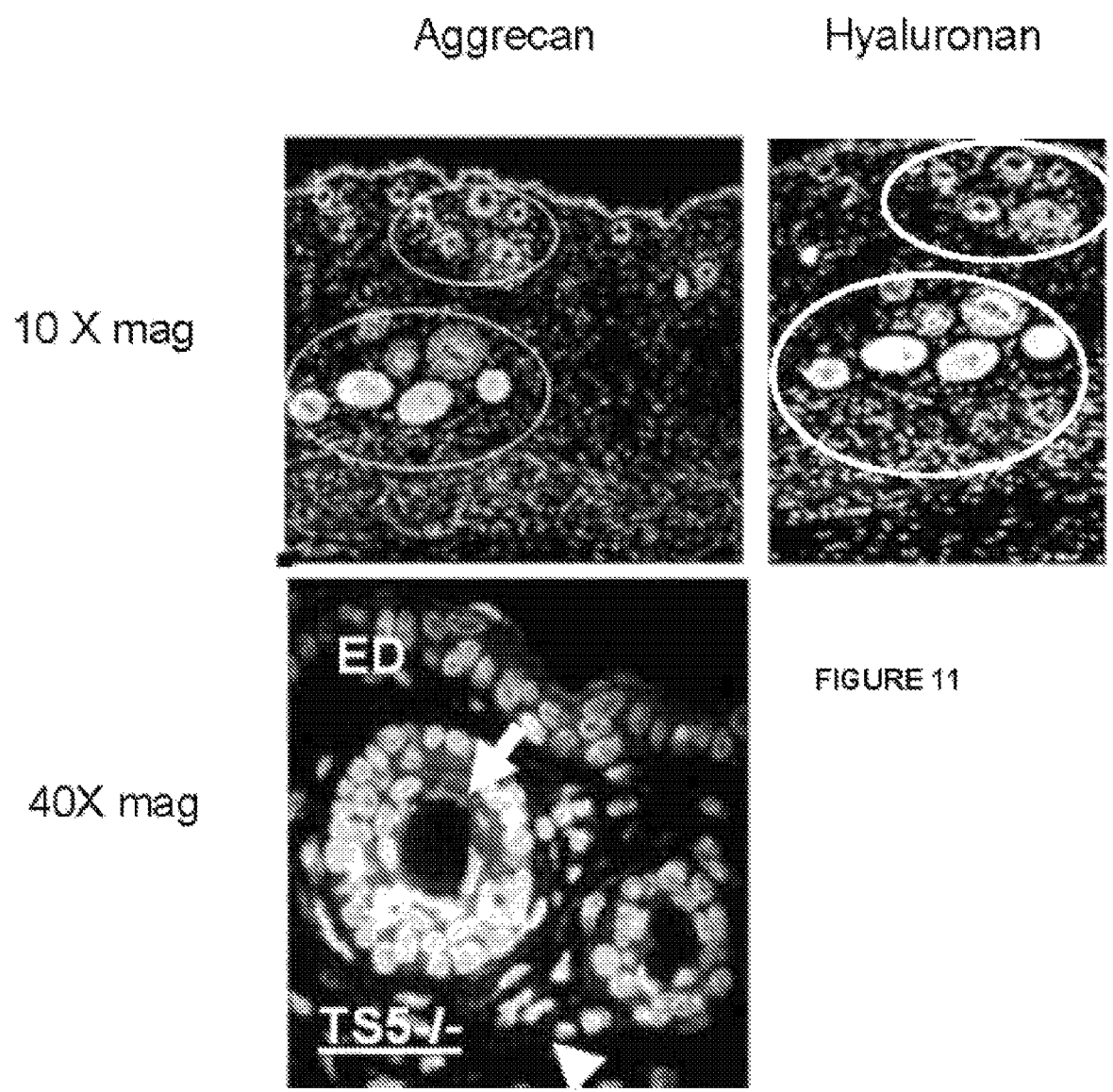

FIG. 11 shows examples of co-localization of aggrecan-hyaluronan complexes in healing dermal wounds of TS5$^{-/-}$ mice.

Figure 12:
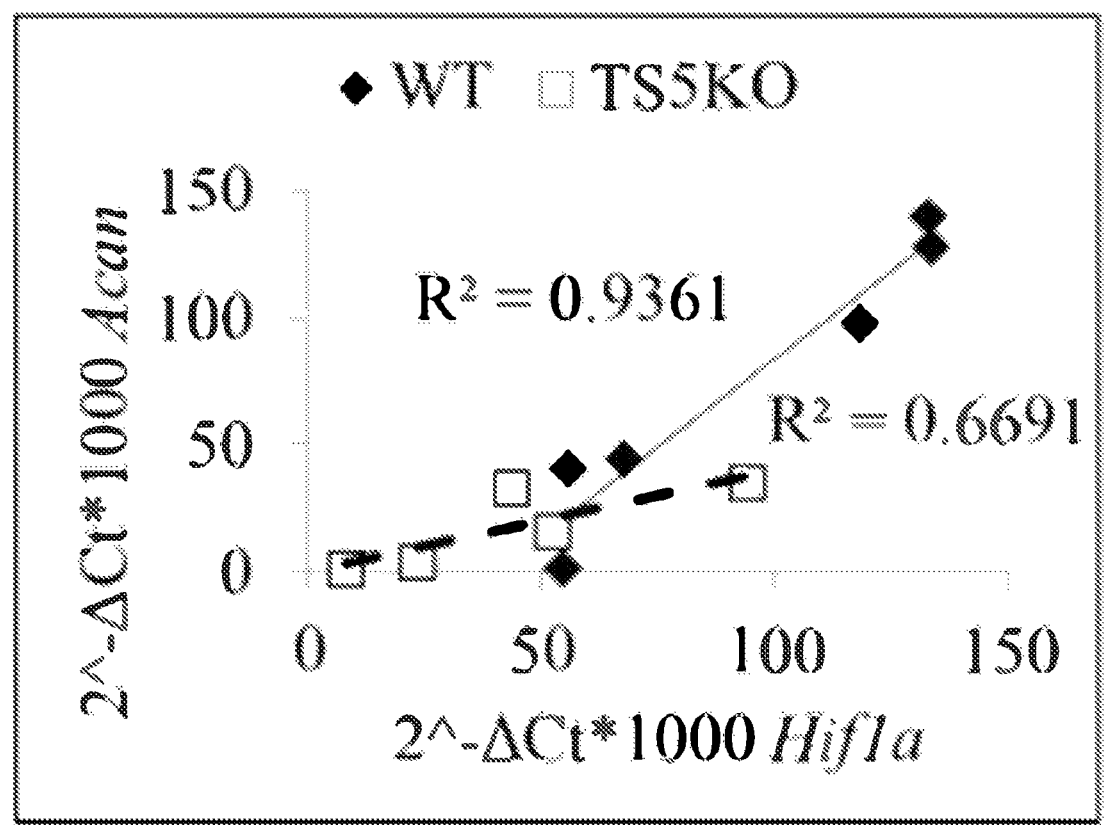
Figure 13:
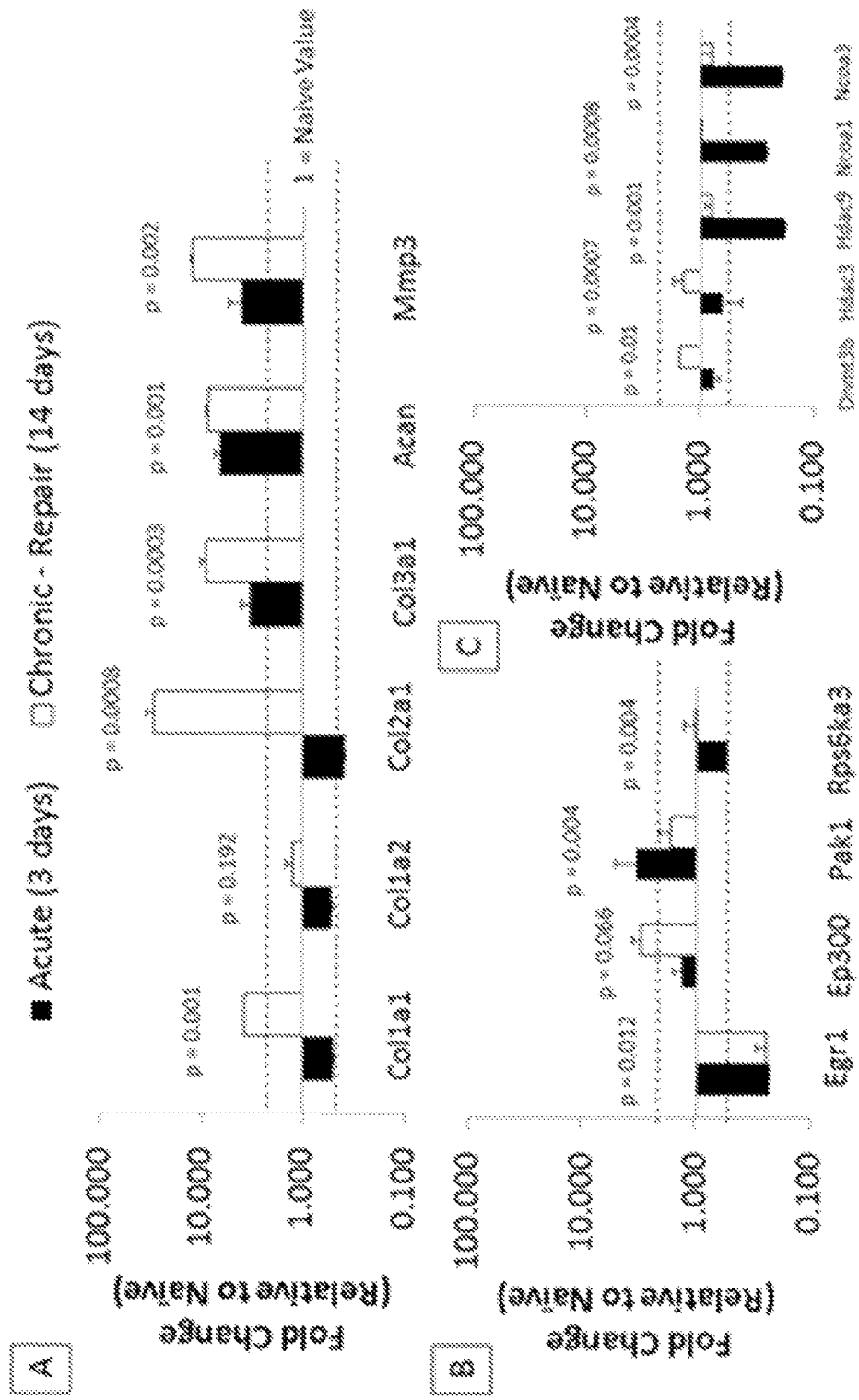

FIG. 12 shows the fold change 2^ ΔΔCT of TGF-β1 injured Achilles tendons relative to Naïve (log scale). Each bar represents a triplicate assay of 3 or 2 pools of n=12 and 20, respectively, with 2 pools for Naïve with n=20 tendons. Dashed lines represent >2 fold up or down regulated, with ANOVA p-values presented. A) Matrix proteins. B) Epigenetics modification genes of interest based on pathway search. C) Epigenetic modification genes that are involved in interactions with genes of interest FIG. 13 shows the correlation in expression of Hif1a and Acan during injury time course.

DETAILED DESCRIPTION

The present invention provides a method for monitoring a treatment for a musculoskeletal disorder and a method of treating a musculoskeletal disorder.

As used herein, the phrase "musculoskeletal disorder" is intended to include all disorders related to bone, joint capsule, muscle, ligaments, and tendons.

The term "biomarker" as used herein, refers to any biological compound that can be measured as an indicator of the physiological status of a biological system. A biomarker may comprise an amino acid sequence and fragments thereof, or a nucleic acid sequence.

"Measuring" or "measurement" means assessing the presence, absence, quantity or amount (which can be an effective amount) of a given substance within a sample, including the derivation of qualitative or quantitative concentration levels of such substances, or otherwise evaluating the values or categorization of a subject's clinical parameters. Alternatively, the term "detecting" or "detection" may be used and is understood to cover all measuring or measurement as described herein.

The term "subject" or "patient" as used herein, refers to a mammal, preferably a human.

The term "treating", "treat", or "treatment" within the context of the instant invention, means an alleviation of symptoms associated with a disorder or disease, or halt of further progression or worsening of those symptoms, or prevention or prophylaxis of the disease or disorder. For example, within the context of this invention, successful treatment may include an alleviation of symptoms related to musculoskeletal disorders or a halting in the progression of the disorder.

Measurement of a biomarker generally relates to a quantitative measurement of an expression product, which is typically a protein or polypeptide. In some embodiments, the measurement of a biomarker may relate to a quantitative or qualitative measurement of nucleic acids, such as DNA or RNA. Expression of the biomarkers may be measured using any method known to one skilled in the art. Methods for measuring protein expression include, but are not limited to Western blot, immunoprecipitation, immunohistochemistry, Enzyme-linked immunosorbent assay (ELISA), Radio Immuno Assay (RIA), radioreceptor assay, proteomics methods, mass-spectrometry based detection (SRM or MRM), Fluorescence Assisted Carbohydrate Electrophoresis (FACE) or quantitative immunostaining methods. Methods for measuring nucleic acid expression or levels may include, but are not limited to Southern Blotting, Northern Blotting, quantitative PCR, dot blotting, FISH or other methods of in situ hybridization.

In some embodiments, two or more biomarkers may be measured to monitor a treatment of a musculoskeletal disorder. In some embodiments, by way of non-limiting example, the two or more biomarkers may include aggrecan and hyaluronan. In some embodiments, the two or more biomarkers may be selected from aggrecan, hyaluronan synthases 1, 2 and 3, Col1a1, Col2a1, Col3a1, Fibronectin, Adamts5 and Mmp3. In some embodiments two or more biomarkers may be selected from Aggrecan (Acan), Hyaluronan synthases 1, 2 and 3, Collagen, type 1, alpha 1 (Col1a1), Collagen, type 2, alpha 1 (Col2a1), Collagen, type 3, alpha 1 (Col3a1), Fibronectin, a disintegrin and metalloproteinase with thrombospondin type 1 motif 5 (Adamts5), Matrix metallopeptidase 3 (Mmp3), Hypoxia inducible factor 1a (Hif1a), Pyruvate kinase, muscle (Pkm), Angiopoietin-like 4 (Angptl4) p21 protein (Cdc42/Rac)-activated kinase 1 (Pak1), Aurora Kinase B (A urkb), Aurora Kinase A (Aurka), N-acetyltransferase ESCO2 (Esco2), Lysine-specific demethylase 5C (Kdm5c) Early growth response 1 (Egr1), E1A binding protein 300 (Ep300), and Ribosomal protein S6 kinase alpha-3 (Rps6ka3) Histone deacetylase 9 (Hdac9), Nuclear receptor coactivator 1 (Ncoa1), and Nuclear receptor coactivator 3 (Ncoa3). In some embodiments, combinations of three, four, five, six, seven, eight, nine, ten or more biomarkers may be used together and may be selected from Aggrecan (Acan), Hyaluronan synthases 1, 2 and 3, Collagen, type 1, alpha 1 (Col1a1), Collagen, type 2, alpha 1 (Col2a1), Collagen, type 3, alpha 1 (Col3a1), Fibronectin, a disintegrin and metalloproteinase with thrombospondin type 1 motif 5 (Adamts5), Matrix metallopeptidase 3 (Mmp3), Hypoxia inducible factor 1a (Hif1a), Pyruvate kinase, muscle (Pkm), Angiopoietin-like 4 (Angptl4) p21 protein (Cdc42/Rac)-activated kinase 1 (Pak1), Aurora Kinase B (Aurkb), Aurora Kinase A (Aurka), N-acetyltransferase ESCO2 (Esco2), Lysine-specific demethylase 5C (Kdm5c) Early growth response 1 (Egr1), E1A binding protein 300 (Ep300), and Ribosomal protein S6 kinase alpha-3 (Rps6ka3) Histone deacetylase 9 (Hdac9), Nuclear receptor coactivator 1 (Ncoa1), and Nuclear receptor coactivator 3 (Ncoa3).

In some embodiments, the expression level of the two or more biomarkers may be measured at about 48 hours post-treatment, about 2 weeks post treatment or at about 4 weeks post treatment. Other times for measurement post-treatment may also be used. By way of non-limiting example, the measurements may be taken at about 1, 2, 3, 4, 5, 6, or 7 days post-treatment and/or at about 1, 2, 3, 4, 5, 6, 7, 8 or more weeks post treatment.

In some embodiments, the treatment may include an exercise therapy and/or an enzymatic therapy. The exercise therapy includes an appropriate exercise for the musculoskeletal disorder being treated. An enzymatic therapy may include one or more enzymes or other compounds that degrade one or more components of a matrix present at a treatment site.

Examples

Tendinopathy Model

Methods

Human studies: Intraoperative tendon specimens (IRB #11122301) were obtained from the proximal origin of the extensor carpi radialis brevis (ECRB) and distal origin of the biceps brachii tendons from patients undergoing surgical debridement for painful tendinopathy.

Figure 1:
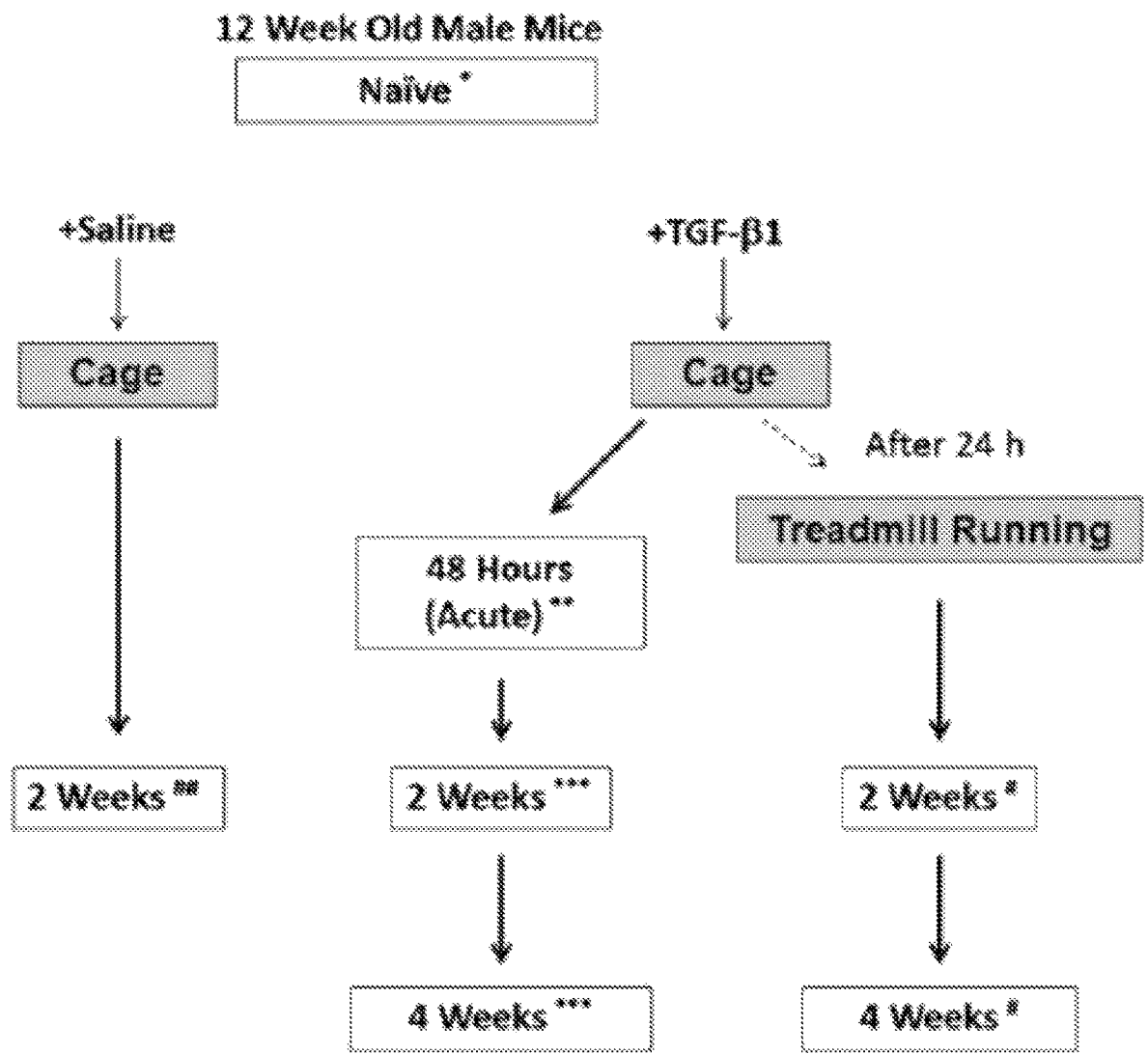
FIG. 1 illustrates a schematic of experimental design. *n=10 mice (20 tendons) for PCR, n=5 mice (8 tendons) for biomechanics, n=3 mice for histology; n=10 for PCR, n=7 for biomech, n=3 for histo; *n=10 for PCR, n=6 for biomech, n=3 for histo; #n=10 for PCR, n=5 for biomech, n=3 for histo; ##n=3 for histo.

Induction of murine tendinopathy: C57Bl6 male mice (12 weeks old) were injected (28 G needle) into the mid-portion of the right Achilles tendon with 100 ng active TGF-β1 (Pepro Tech Inc) in 6 μL of 0.1% (v/w) BSA in saline. The study design included naïve (uninjured) controls, an acute response group (48 h post-injection), and mice which received cage or treadmill activity (FIG. 1).

Mechanical Stimulation

At 24 h post-injection, mice began uphill (17 degrees) treadmill running (Stoelting/Panlab at 32 cm/s, 20 min/day, 5 days per week (Li et al., 2011) for 2 or 4 weeks.

Geometry and Mechanical Testing

The Achilles tendon-calcaneus complex was dissected and the calcaneus potted in methyl methacrylate. Tendon cross-sectional area (CSA) was measured using a precision caliper (for width) and a laser displacement sensor (for thickness), assuming a rectangular geometry (Wang et al., 2012). Material testing was conducted at a plantar flexion angle of 45° (Wang et al., 2006) with the specimen in an isotonic saline bath at 37° C. Each tendon was preloaded to 0.05N, followed by preconditioning (0.05-0.55 N at 0.1 N/s for 20 cycles), a five minute recovery in an unloaded state, a static stress relaxation test (5% strain at 2.5%/s, held for 600 s), and a load to failure test at 0.5%/s.

Histology and Immunohistochemistry (INC)

Following fixation, decalcification, and paraffin embedding, the Achilles tendon-bone complex was sectioned longitudinally and stained with Safranin O (Wang et al., 2012). The number of cells per 350×300 μm$^2$ field was counted using Image J (NIH), for each of four stained images per tendon specimen, by two investigators blinded to the treatment group. For IHC, deparaffinized sections were incubated with the following primary antibodies (10 μg/ml) overnight at 4° C.: high molecular weight aggrecan core protein (anti-DLS, Plaas et al., 2007), ADAMTS5 (anti-KNG, Plaas et al., 2007), collagen I (Abcam ab-34710) and collagen III (Abcam, ab-7778). Sections were counterstained with methyl green.

Quantitative PCR (QPCR)

The tendon proper (i.e. excluding calcaneal insertion and proximal myotendinous junction) was dissected fresh and placed in RNALater™ (Qiagen) at −20° C. For RNA isolation, 20 tendons, pooled for analysis of each experimental group, were combined in liquid nitrogen, fragmented in a Bessman Tissue pulverizer, and extracted in 1 ml of Trizol™ (Life Technologies) by vortexing for 60 s. RNA was purified with an RNeasy Mini Kit™ (Qiagen) and yields of RNA were approximately 50 ng per tendon. cDNA was synthesized using the Super Script First-Strand Synthesis Kit™ (Life Technologies) using 1 μg of RNA. All primers were from Life Technologies, Inc.: Acan (Mm00545794_m1); Adamts5 (Mm01344180_m1); Gapdh (Mm99999915_g1); Col1a1 (Mm00801666_g1); Col2a1 (Mm01309565_m1); Col3a1 (Mm00802331_m1); Mmp3 (Mm00440295_m1); and Fn1 (Mm01256744_m1). Amplifications were performed in triplicate with an Applied Biosystems 7300 Real-Time PCR System as follows: 50° C., 2 min; 95° C., 10 min; 95° C., 15 s; 60° C., 1 min; repeated 39 times (Velasco et al., 2011). Data was processed as ΔCt (relative to Gapdh) for each gene at each time point, to provide relative transcript levels and fold-change was calculated as $2^{-\Delta\Delta Ct}$ relative to the comparison group specified.

Statistical Analysis

Biomechanical, cell counting, and gene expression results were compared across time points using one-way ANOVA with Tukey's post-hoc tests (SPSS17, IBM, Armonk, N.Y.). To test the study hypothesis, at each time point, an unpaired, two-tailed Student's t-test was used to compare data from the cage and treadmill groups.

Results

Striking histopathologic similarities between human and murine tendinopathy. Images from naïve murine Achilles, 48 h following TGF-β1 injection, and normal human patellar tendon exhibited the same, essentially GAG-free, linear organization of collagen fibers and cells. Typical images from TGF-β1 injected murine tendons illustrate that at both 2 and 4 weeks, tendons showed pericellular and interfibrillar accumulation of GAG, an increase in chondrocyte-like cells, and a loss of parallel arrangement of collagen fibers in and around GAG-enriched areas. Of particular note, the development of these pathological features required the injection of TGF-β1, since injection of saline/BSA did not result in any marked changes in cell morphology or matrix appearance at 2 weeks. Histopathologic features of the affected 4-week murine tendons were also seen in tendinopathic human extensor carpi radialis longus (ECRB) and biceps samples (Bell et al., 2013a).

Decreased Tensile Properties Following TGF-β1 Injection and Cage Activity

Figure 2:
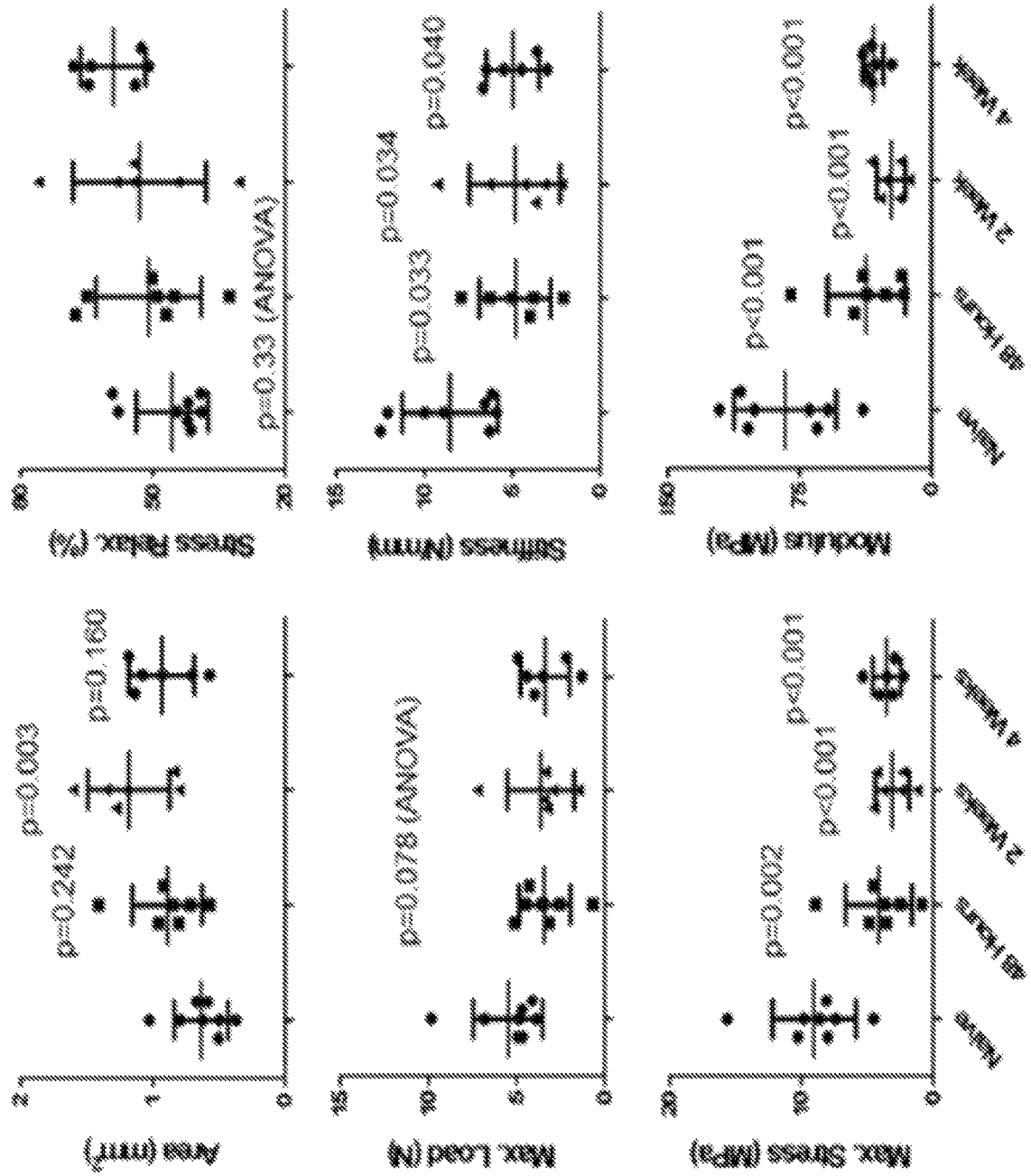
FIG. 2 illustrates the effect of TGF-$\beta$1 injection and cage activity on Achilles tendon mechanical properties. The scatter plots show data for individual tendons in each group, while the p-values correspond to the comparison between means of the experimental and naïve mice. For each time point, horizontal lines denote mean±one standard deviation.

At all times (48 h, 2 and 4 weeks) post-TGF-β1 injection, significant reductions in stiffness (~43%), maximum stress and tensile modulus (greater than 53%) were seen, along with an increase in CSA of ~86% at 2 weeks (FIG. 2 and Table 1). There were no significant differences in stress relaxation or maximum load, despite a trend towards an increase in stress relaxation at 4 weeks (p=0.07), and a trend towards a decrease in maximum load at 48 h and 4 weeks (p=0.09).

Effect of TGF-β1 Injection and Cage Activity on Gene Expression

The ΔCt values for naïve mice (Table 2) indicate that the order of transcript levels is Col1a1>Fn>Col3a1>Acan>Col2a1 which appears to be consistent with the matrix composition of normal midsubstance tendon. Furthermore, consistent with known effects of TGF-β1 on both chondrogenic and fibrogenic signaling in dermal fibroblast (Velasco et al., 2011), the expression of matrix genes at all time points (except for Col3a1 at 4 weeks and Co2a1 at 48 h), were significantly elevated (p<0.05) relative to naïve tendons. The fold-change in expression of fibrogenic genes (FIG. 3) showed that the patterns for Col1a1, Col3a1 and Fn1 were similar, with limited activation by TGF-β1 at 48 h, peak activation at 2 weeks and a trend toward reduction to naïve levels at 4 weeks. However, the activation of chondrogenic genes appeared to be relatively delayed, with a progressive increase in Col12a1 expression up to 4 weeks post-injection, and the fold-activation of Acan expression being markedly higher than that for fibrogenic genes at both 2 weeks and 4 weeks.

Treadmill Exercise Following TGF-β1 Injection Increases Tensile Properties and Alters Gene Expression in WT Mice.

Figure 4:
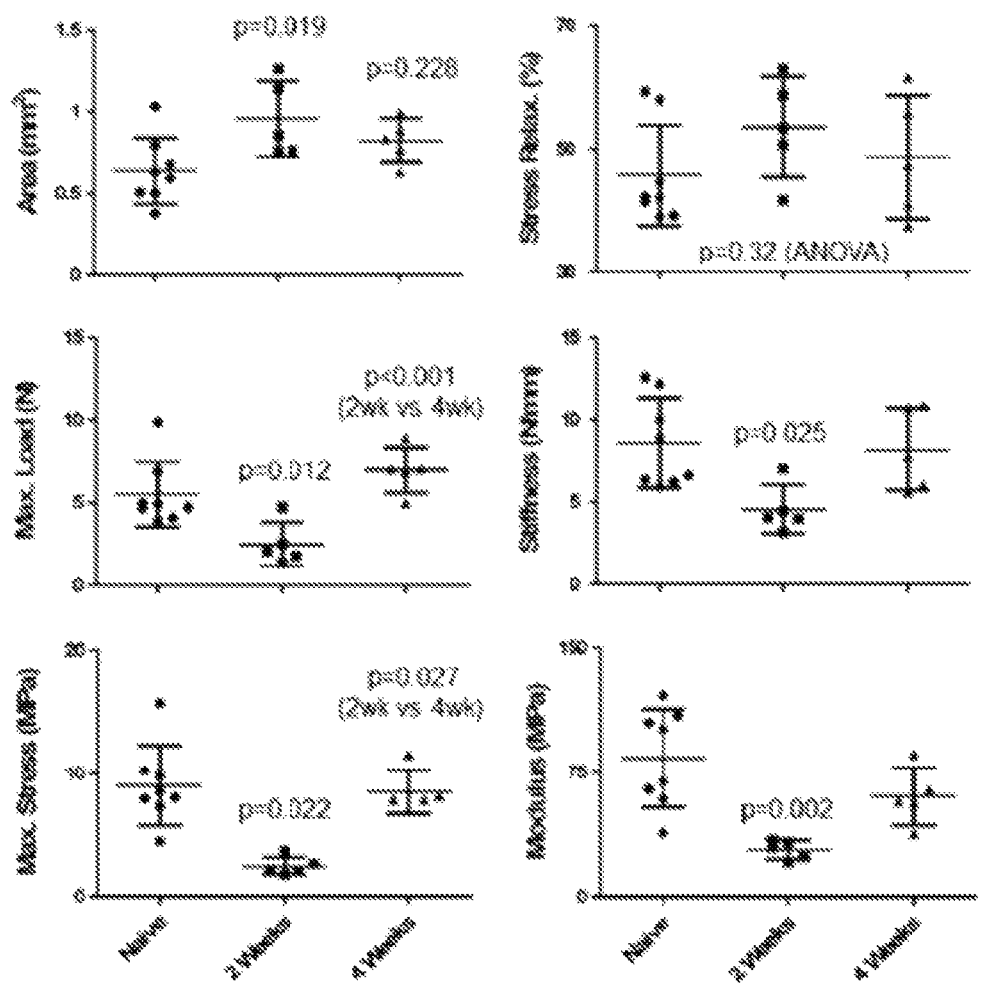
FIG. 4 illustrates the effect of treadmill exercise following TGF-$\beta$1 injection on tendon mechanical properties. The scatter plots show data for individual tendons in each group, while the p-values correspond to the comparison between means of the experimental and naïve mice. For each time point, horizontal lines denote mean±one standard deviation.
Figure 5:
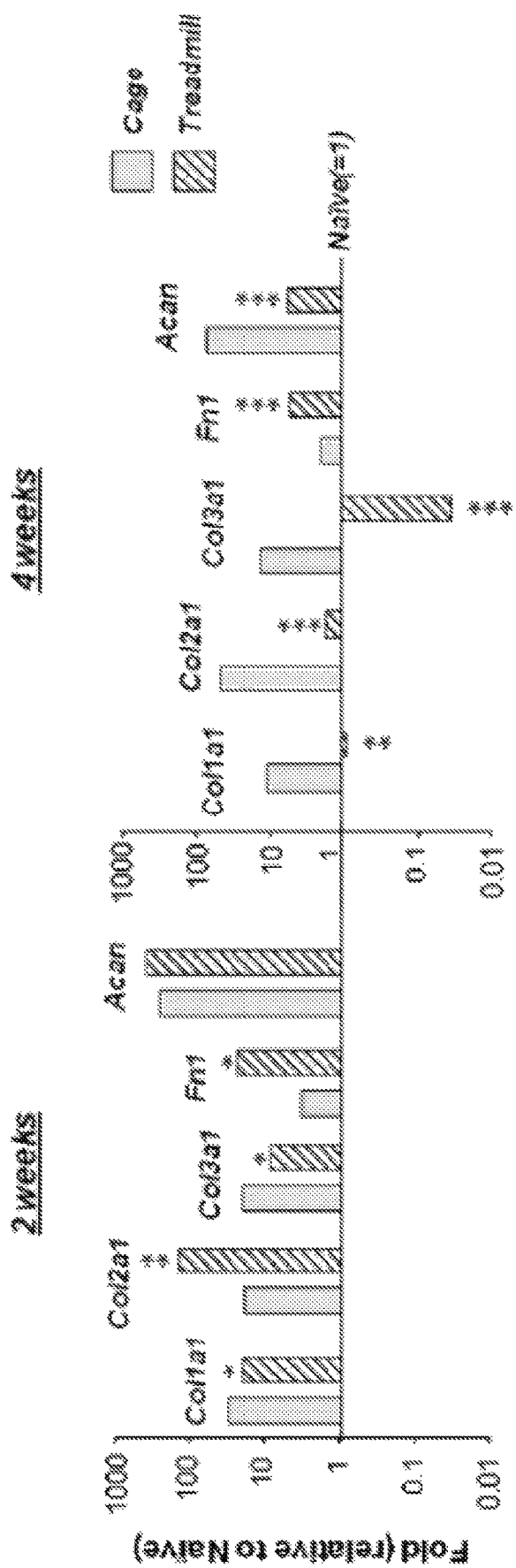
FIG. 5 illustrates the effect of treadmill exercise following TGF-$\beta$1 injection on gene expression. The fold-change in expression of Col1a1, Col2a1, Col3a1, Fn1 and Acan relative to naïve tendons. P-values correspond to the comparison between means of caged and treadmill-run mice for each gene. * denotes $p<0.05$,  denotes $p<0.001$, and * denotes $p<0.0005$.

Two weeks following injection, similar mechanical properties were noted between cage and treadmill exercise groups (FIG. 4 and Table 3). Notably, however, exercise for 4 weeks was effective in restoring biomechanical properties for WT mice. (Table 3). Specifically, it led to recovery in maximum load, stiffness, maximum stress and tensile modulus (p<0.04 in all cases, relative to 2 weeks). At 2 weeks, relative to no exercise, there was a minor, but significant (p<0.05) reduction in the expression of Col1a1 and Col3a1, an increase (p<0.05) of Col2a1 and Fn1 expression, and no significant change in Acan expression (FIG. 5). Following 4 weeks of exercise, there were further marked changes in gene expression. Firstly, relative to cage activity, at 4 weeks there was a 10-fold reduction in expression of Col1a1 (p=0.014) and a 200-fold reduction in Col3a1 (p<0.0001). Moreover, the high expression of Col2a1 and Acan seen with exercise at 2 weeks was reduced by ~25-fold (p=0.0004) and ~12-fold (p<0.001) respectively at 4 weeks. The effect of treadmill exercise was also evident in the cellularity of the injected tendons. Naïve tendons had 305±33 cells per unit area, which was increased by approximately 1.7-fold (519±9) and 2.1-fold (652±95) at 2 weeks and 4 weeks, respectively, in mice maintained at cage activity. However, with treadmill exercise the corresponding increases were significantly lower at 1.3-fold (396±18, p<0.0001) at 2 weeks and 1.6-fold (495±56, p=0.008) at 4 weeks.

Effects of TGF-β1 Injection and Treadmill Exercise on Adamts5 and Mmp3 Expression in WT Mice.

Figure 6:
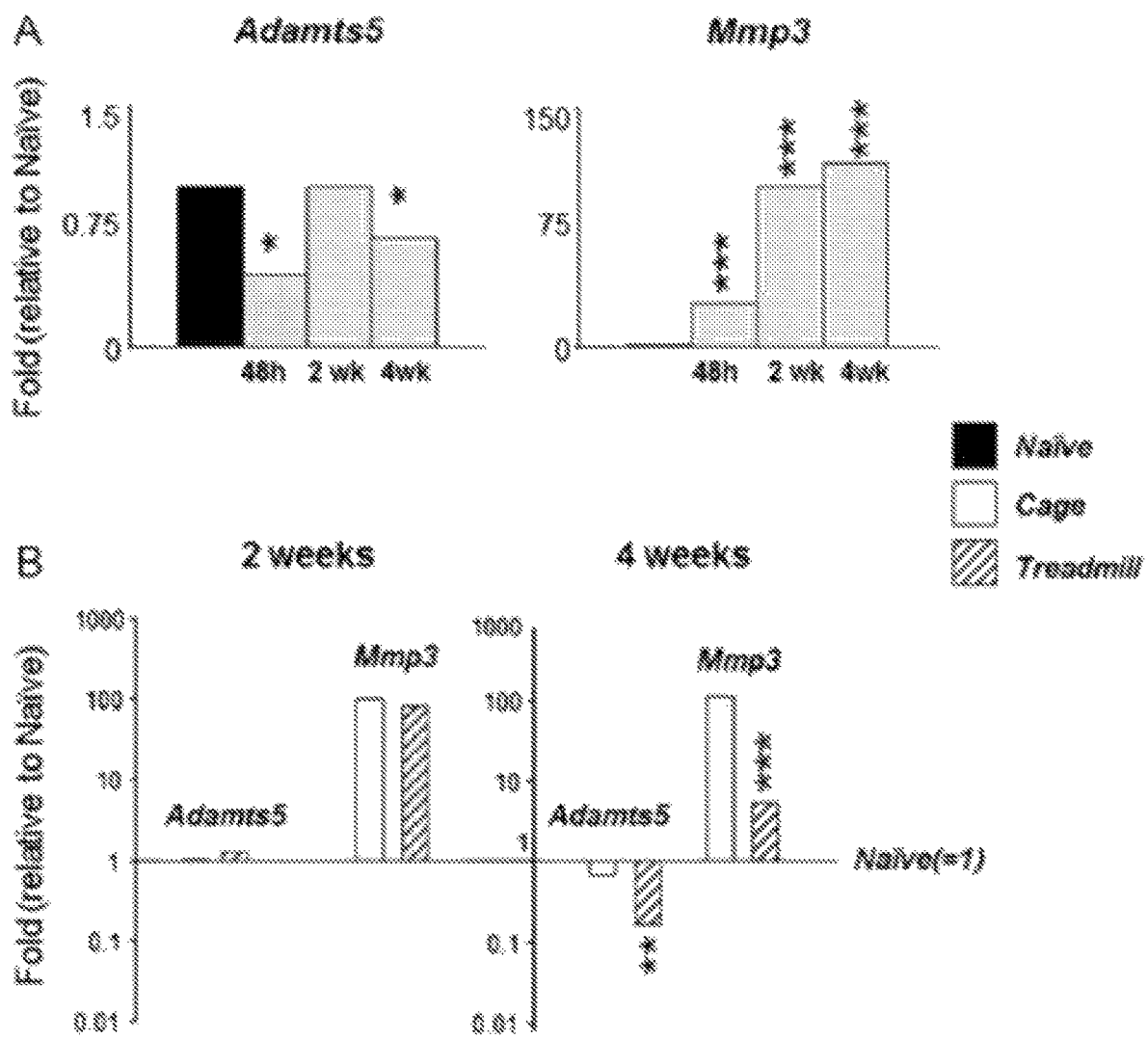
FIG. 6 illustrates the effect of treadmill running following TGF-$\beta$1 injection on gene expression of Adamts5 and Mmp3 (A). The fold-change in expression of Adamts5 and Mmp3 relative to naïve tendons following TGF-$\beta$1 injection and cage activity. * denotes $p<0.05$,  denotes $p<0.001$, and * denotes $p<0.0005$. (B). The fold-change in expression of Adamts5 and Mmp3 relative to naïve tendons, following TGF-$\beta$1 injection and treadmill * denotes $p<0.05$,  denotes $p<0.001$, and * denotes $p<0.0005$.

The exercise-dependent reduction in gene expression seen between 2 and 4 weeks (FIG. 5) was also evident for Adamts5 and Mmp3 (FIG. 6). Without exercise, Adamts5 expression was not markedly affected at any time, whereas Mmp3 was activated ~25-fold at 48 h and further activated to ~110-fold after 2 and 4 weeks. Exercise for 2 weeks had no major effect on expression of either gene, however exercise for 4 weeks decreased Adamts5 (p=0.003) and Mmp3 expression (p=0.003).

Effects of TGF-β1 Injection and Treadmill Exercise on the Abundance of Collagens I and III, Aggrecan and ADAMTS5 in WT Mice.

The major increase in Col1a1, Col3a1 and Acan expression following 2 weeks of cage activity was reflected in increased cell-associated staining. The absence of change in Adamts5 expression at 2 weeks was nonetheless accompanied by a marked increase in protein staining. Conversely, the decreased expression of these genes seen after 4 weeks of exercise (FIGS. 5 and 6) did not appear to markedly alter the abundance of these components.

Effects of TGF-β1 Injection and Treadmill Exercise on Cell Shape and Distribution of Collagens I and III, Aggrecan and ADAMTS5 in WT Mice.

The staining for all components except collagen I was primarily in the pericellular space, suggesting that the IHC procedure detects newly synthesized molecules (Li et al., 2012). For collagen I, staining was also widely distributed throughout the matrix, indicating that both new and resident molecules were detected. In the naïve tissue, collagen I staining was robust throughout the matrix and in the vicinity of individual cells, whereas aggrecan was detected as a diffuse pericellular coat surrounding groups of tenocytes. It is notable that there is staining for aggrecan in naïve tendons, despite the very low, but detectable, transcript levels. Aggrecan is also present in naïve mature mouse FDL tendon, as shown by Western analysis (Wang et al., 2012) suggesting that it largely represents molecules synthesized and retained during development and maturation of the tendon. Conversely, collagen III and ADAMTS5 proteins were not detected in naïve tendons. At 48 h after TGF-β1 injection there was a robust increase in pericellular staining for both collagen III and ADAMTS5, but no clear change for either aggrecan or collagen I. Of interest, the increase in ADAMTS5 staining occurred in the absence of a change in expression, suggesting that post-translational events control its tissue abundance. After 2 weeks of cage activity, collagens I and III, aggrecan and ADAMTS5 all showed increased staining in the cell-associated matrix, which was less evident after 2 weeks of treadmill exercise. The most notable difference between cage and exercised groups was the shape and organization of the cells. Cage activity for 2 or 4 weeks resulted in groups of rounded cells, with enlarged and rounded nuclei, and with each cell surrounded by its own organized pericellular matrix. In contrast, treadmill exercise prevented the appearance of such chondrogenic groups at both times, such that resident cells exhibited the flat nuclei and elongated tenocyte morphology seen in naïve tendons. Moreover, due to the lack of an organized pericellular matrix, these elongated cells appeared to be interconnected and directly associated with the adjacent collagen fibers. The overall abundance and distribution of ADAMTS5 protein under each condition, was compared to staining for the aggrecanase product, G1-NITEGE. Both antigens showed an increased abundance in TGF-β1-injected tendons, and while the ADAMTS5 was confined to the cells, the G1-NITEGE was also abundant in the tendon matrix. However, many more cells stained for G1-NITEGE than ADAMTS5, suggesting the activity of other aggrecanases in the tendon.

Figure 3:
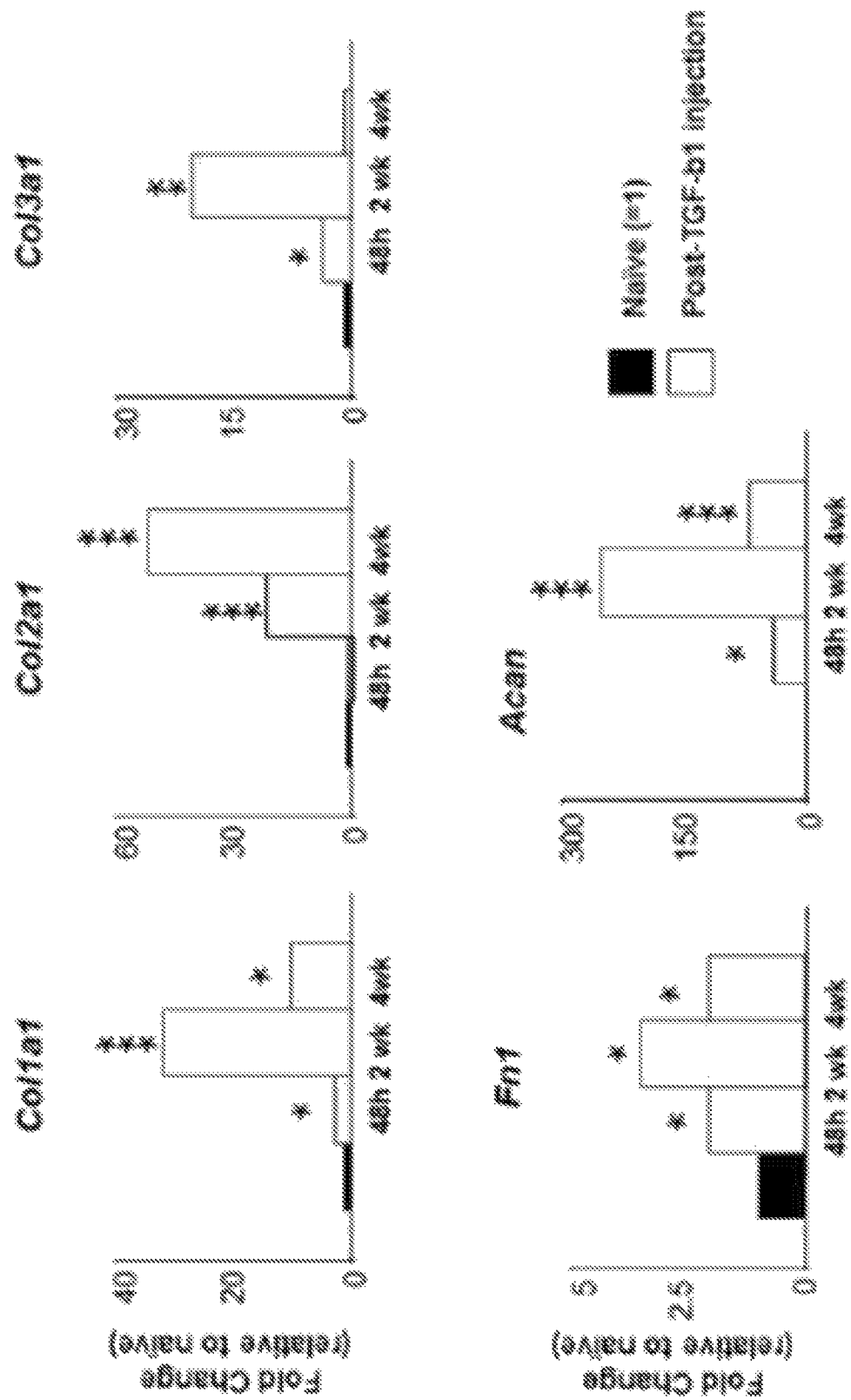
FIG. 3 illustrates the effect of TGF-$\beta$1 injection and cage activity on expression of genes for matrix proteins. The fold-change in expression of Col1a1, Col2a1, Col3a1, Fn1 and Acan relative to naïve tendons. * denotes $p<0.05$,  denotes $p<0.001$, and * denotes $p<0.0005$.

A murine model of tendinopathy has been developed that closely mimics the human pathology, and is also amenable to testing new therapeutic interventions. Firstly, the impairment of mechanical properties (FIG. 2) is consistent with the finding that human Achilles tendinopathy results in inferior mechanical properties (Arya and Kulig, 2010). Secondly, histopathologic findings such as hypercellularity, chondroid deposition and collagen disorganization, strongly resemble human tendinopathies. Thirdly, activation of aggrecan gene expression in the model (FIGS. 3 and 5) has also been reported in human Achilles tendinopathy (Corps et al., 2006; de Mos et al., 2009). Perhaps the most important authentication of the model is the finding that controlled exercise can reverse over-expression of Acan, Col1a1, Col2a1, Col3a1 and Mmp3, and essentially eliminate chondroid accumulation. Moreover, this is accompanied by full recovery of tendon tensile properties, which supports clinical outcomes of exercise regimens (Silbernagel et al., 2011) and permits future quantitative therapeutic studies. One advantage of this novel model is that tendinopathy is induced simply by injection of TGF-β1 into the midsubstance. The rationale for this derives from both clinical and bench studies indicating that excess active TGF-β1 in tendons is pathogenic. Analysis of tendinopathic Achilles (Pingel et al., 2012) showed increased expression of TGF-β1 associated with increased cellularity and collagen disorganization. Further, treatment of repair sites with antibodies to TGF-β1 (Chang et al., 2000) potentiated repair, whereas TGF-β1 generated by tendon transection was pathogenic (Maeda et al., 2011). In our model, tensile properties correlated with changes in cell morphology, gene expression and abundance and localization of matrix proteins and ADAMTS5. The relationship between these parameters and tendinopathy was most apparent when comparing tendinopathic with exercised mice. At 2 weeks, the lowest values of maximum stress were observed (FIG. 2), and coincided with high abundance of chondroid cells and highest expression of Acan, Col1a1, Col3a1 and Fn (FIG. 3). Further, in the absence of exercise these abnormalities remained largely unchanged. However, in mice exercised for 4 weeks, maximum stress recovered to naïve levels, chondroid cells were reduced and expression of Acan, Col1a1, Col2a1 and Col3a1 essentially returned to levels of naïve tendon (FIG. 5). Moreover, exercise reduced the expression of Mmp3 to near naïve levels and expression of Adamts5 to levels well below naïve (FIG. 6).

Adamts5$^{-/-}$ Model with Tendinopathy

Methods

Animals:

C57Bl6 mice were bred in-house and all studies received IACUC approval. TS5$^{-/-}$ mice were generated by excision of exon 2 to delete the catalytic site (Malfait et al. 2010), and phenotypic traits of this colony have been described in relation to mechanical allodynia, (Malfait et al. 2010) joint cartilage repair (Li et al. 2011), dermal repair, (Velasco et al. 2011) and tendon structure function properties. (Wang et al. 2012) Tendinopathy induction: As described previously (Bell et al. 2013a, 2013b), mice were injected into the mid-portion of the right Achilles tendon with 100 ng hrTGF-β1 (Active Form, PeproTech Inc., Rocky Hill, N.J.) in 6 μl of sterile saline containing 0.1% ultrapure BSA (Sigma Aldrich, St. Louis, Mo.). Mice were sacrificed at 48 h (acute response), 2 or 4 weeks following TGF-β1 injection; a separate group of noninjured control (i.e., naïve) mice was included for comparison. Mechanical stimulation: Mice were subjected to uphill (17°) running on a Stoelting/Panlab treadmill at 32 cm/s for 20 min/day for 5 days/week, starting 1 day after TGF-β1 injection. (Bell et al., 2013a, 2013b) A control group of cage (i.e., no treadmill) activity mice was examined at 4 weeks post-injection. Biomechanical testing of Achilles tendons was performed as described. (Wang et al. 2012, Bell et al. 2013a) Gait analysis of TS5$^{-/-}$ and wild type (WT) mice was conducted at baseline (3 days prior to injection) and at 2, 3, and 4 weeks post-injection using a TreadScan system (CleverSys Inc., Reston, Va.). For each mouse, gait parameters were normalized to its baseline value. (Plaas et al. 2011) Quantitative PCR: Tendons (n=20 pooled per experimental group) were harvested and stored at 20° C. in RNALater (Qiagen, Valencia, Calif.). RNA was isolated and primers for the Taqman assay were from Life Technologies (Grand Island, N.Y.) as previously described (Bell et al., 2013a); primers were also obtained for Itga1 (Mm01306375_m1), Itga2 (Mm00434371_m1), (Mm01309565_m1), Itga5 (Mm00439797_m1), ItgaV (Mm00434506_m1), Itgb1 (Mm01253230_m1), Itgb3 (Mm00443980_m1), and Itgb5 (Mm00439825_m1). Histology and immunohistochemistry (IHC): Lower hind limb samples were prepared as described previously. (Bell, et al., 2013a, Li et al. 2012) Antibodies to collagen types I and III were from Abcam (Cambridge, Mass.); aggrecan was detected with anti-DLS as described. (Wang et al. 2012, Bell et al. 2013a) Skin sections, at 15 days post-wounding in TS5$^{-/-}$ mice were stained for confocal microscopy as described previously. (Velasco et al., 2011) Statistical analyses: Biomechanical properties and gene expression data were compared across time points using a one-way ANOVA (SPSS 17; IBM). Temporal gait results were assessed using one-way ANOVA with repeated measures. Post-hoc Tukey's tests were used for pairwise comparisons, and significance was assumed for $p<0.05$.

Results

Figure 7:
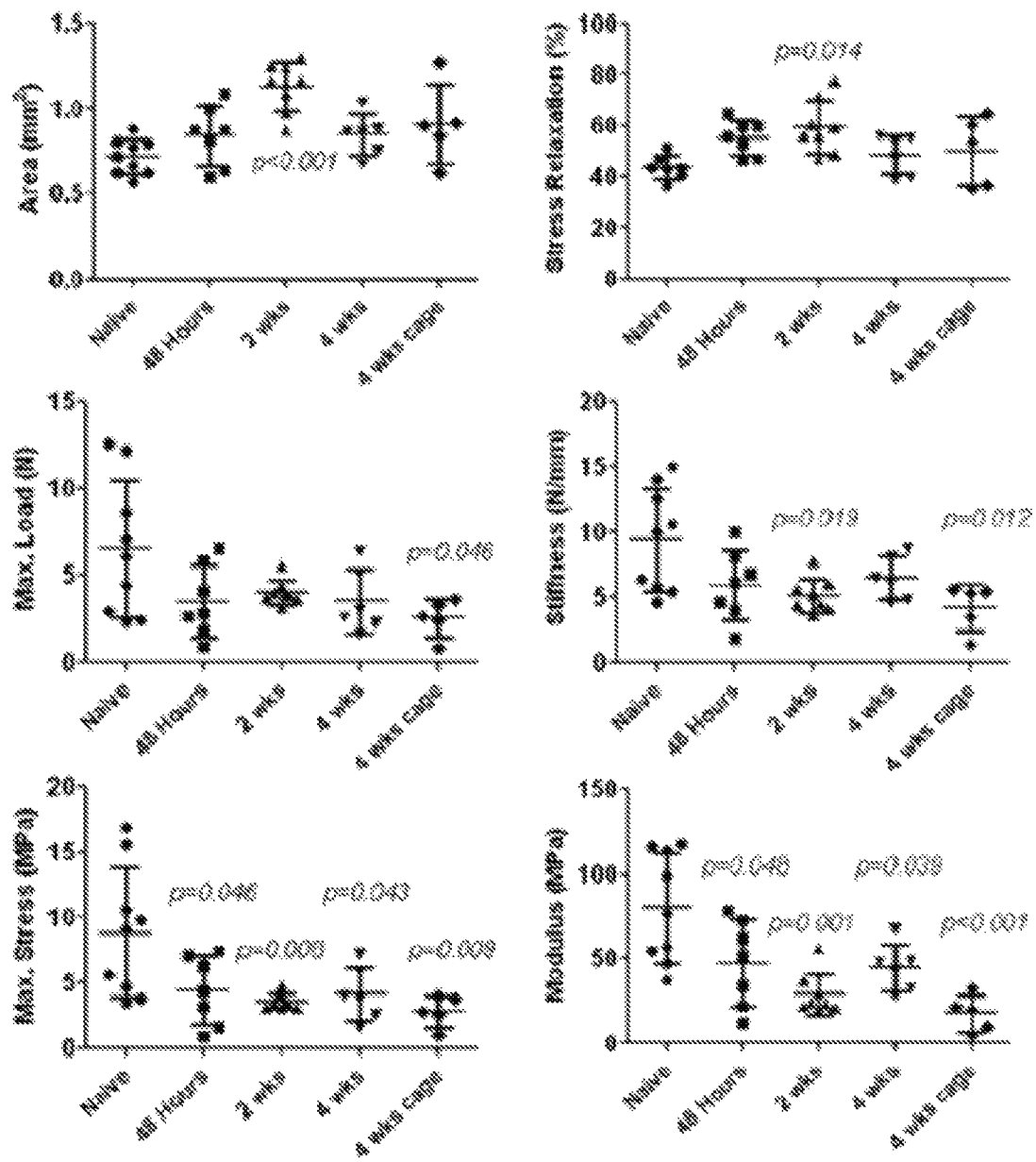
FIG. 7 illustrates the effect of TGF-$\beta$1 with treadmill on Achilles tendon mechanical properties in TS5$^{-/-}$ mice. The scatter plats show data for individual tendons within each experimental group (naïve, n=9; 48 h treadmill, n=7; 2 weeks treadmill, n=8; 4 weeks treadmill, n=6; 4 week cage, n=5). P-Values correspond to the comparison (post-hoc Tukey's test) between means of the respective experimental group and naïve mice. For each time point, horizontal lines denote mean±1 standard deviation.

Absence of TS5 Prevents Treadmill-Induced Recovery of Achilles Biomechanical Strength Tendon maximum load, stiffness, maximum stress, and tensile modulus all exhibited reductions, relative to naïve mice, following TGF-β1 injection of TS5$^{-/-}$ mice. Maximum stress and modulus exhibited significant differences relative to uninjured tendons at each healing time point (FIG. 7), with sustained impairment of these tendon properties observed up to 4 weeks post-injection. Tendon cross-sectional area increased significantly at 2 weeks post-injection and then returned to naïve levels at 4 weeks. Comparison of results for treadmill and cage activity mice at 4 weeks post injection revealed no differences ($p>0.28$ for all mechanical and geometric outcomes).

The Non-Reparative Phenotype of TS5$^{-/-}$ Mice is Accompanied by a Major Deficiency in Expression of Tendon Collagens Comparison of gene expression levels in Achilles tendons of naive WT and naïve TS5$^{-/-}$ mice (Table 4) showed that the order of transcript abundance was similar in each genotype (Col1a1>Fn1>Col3a1>Col2a1>Acan). However, there were major differences in absolute values, with Col3a1 and Col1a1 more abundant in WT (~20- and ~4-fold respectively, $p\leq0.0001$) and Col2a1 and Acan more abundant in TS5$^{-/-}$ (~60- and ~5-fold respectively, $p<0.01$). This difference in naive mice is consistent with the finding that the flexor digitorum longus (FDL) and Achilles tendons of naive TS5$^{-/-}$ mice contain aggrecan-rich deposits (ARDS), which adversely affect their biomechanical properties. (Wang et al. 2012.) Another genotypic difference was in the time course of the response of individual genes to TGF-β1 injection (Table 4). In WT mice, all genes showed maximum expression at 2 weeks, except for Col2a1 which peaked at 4 weeks. However, for TS5$^{-/-}$ mice the maximum expression was generally earlier; for Col2a1 it was in naive mice, for Col3a1 and Acan at 48 h, and for Col1a1 and Fn1 at 2 weeks, suggesting that the absence of TS5 resulted in a more rapid response to TGF-β1 injection overall.

Figure 8:
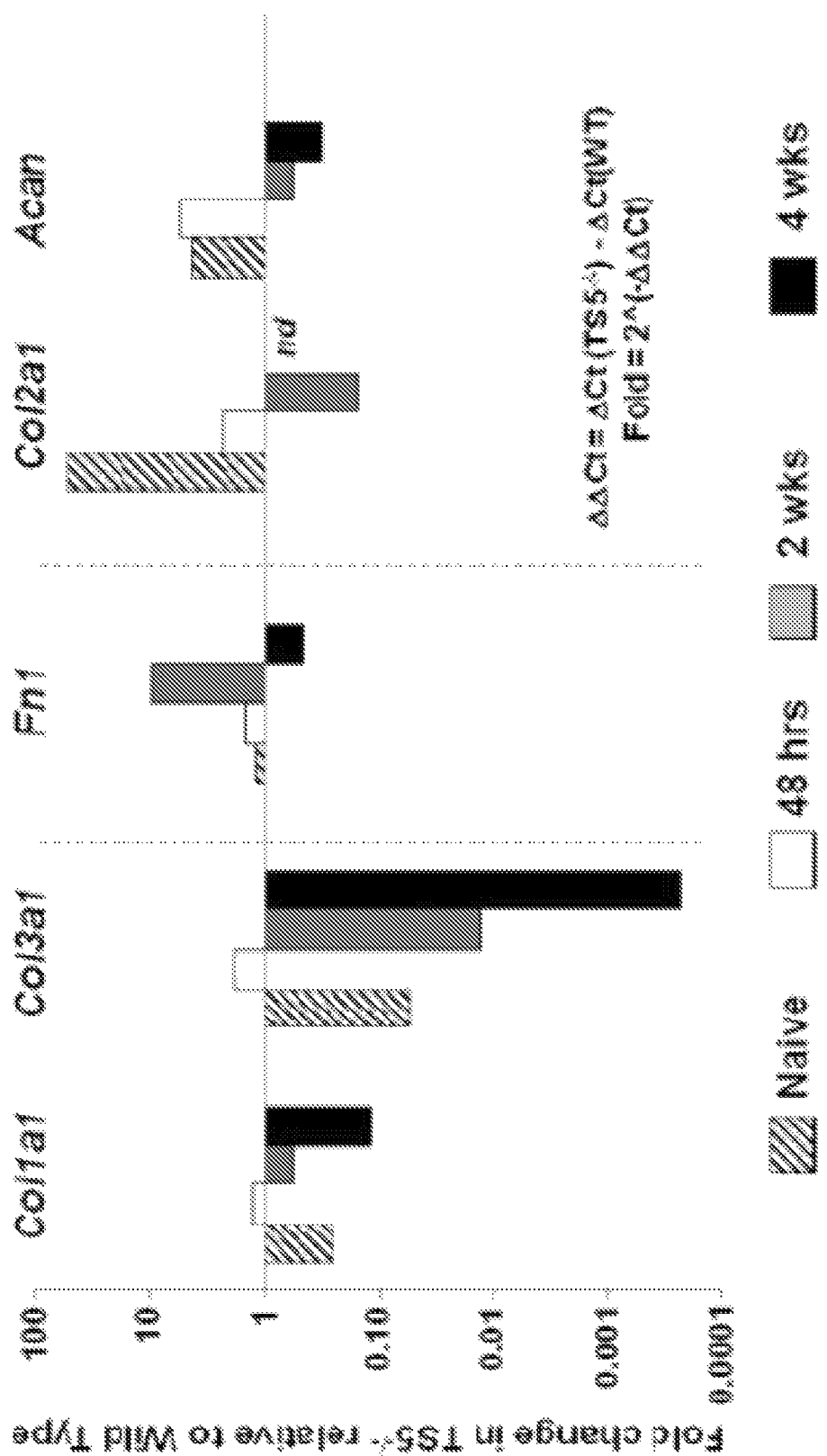
FIG. 8 illustrates the effect of TGF-$\beta$1 and treadmill on matrix gene expression in Achilles from WT relative to TS5$^{-/-}$ mice. Data for each experimental group were obtained from a pool of 20 tendons. The $\Delta$CT values obtained from TS5$^{-/-}$ mice were reduced by the $\Delta$CT values for the equivalent WT samples to generate a $\Delta\Delta$CT value, and the fold difference was calculated as $2^{-\Delta\Delta Ct}$ where the WT value was set at unity. Values above and below unity indicate a higher and lower fold-increase in the TS5$^{-/-}$ mice relative to WT respectively.

However, the major distinction between WT and TS5$^{-/-}$ mice was in the extent of the change in transcript abundance for each gene. It was found (FIG. 8) that for both Col1a1 and Col3a1 the response in the TS5$^{-/-}$ mice was markedly lower, particularly for Col3a1 which was about 100- and 1,000-fold lower at 2 and 4 weeks, respectively. Given that the absolute expression levels in naive mice for Col3a1 were markedly lower for TS5$^{-/-}$ relative to WT (Table 4), tendinopathy was associated with a severe deficiency in Col3a1 expression in TS5$^{-/-}$ tendons. For Fn1 the fold-change was similar between genotypes, although greater in TS5$^{-/-}$ mice at 2 weeks, and for Acan and Col2a1, both of which had higher naïve values in the TS5$^{-/-}$ mice, the fold-change was relatively minor for both genotypes and the response pattern was similar for both genes (FIG. 8). Since the tensile properties of tendons are largely attributable to the abundance, cross-linking and linear organization of collagens type I and type III, the inability of TS5$^{-/-}$ mice to reverse the tendinopathy appears to be at least partly explained by the very low expression of Col3a1 at 2-4 weeks.

Figure 9:
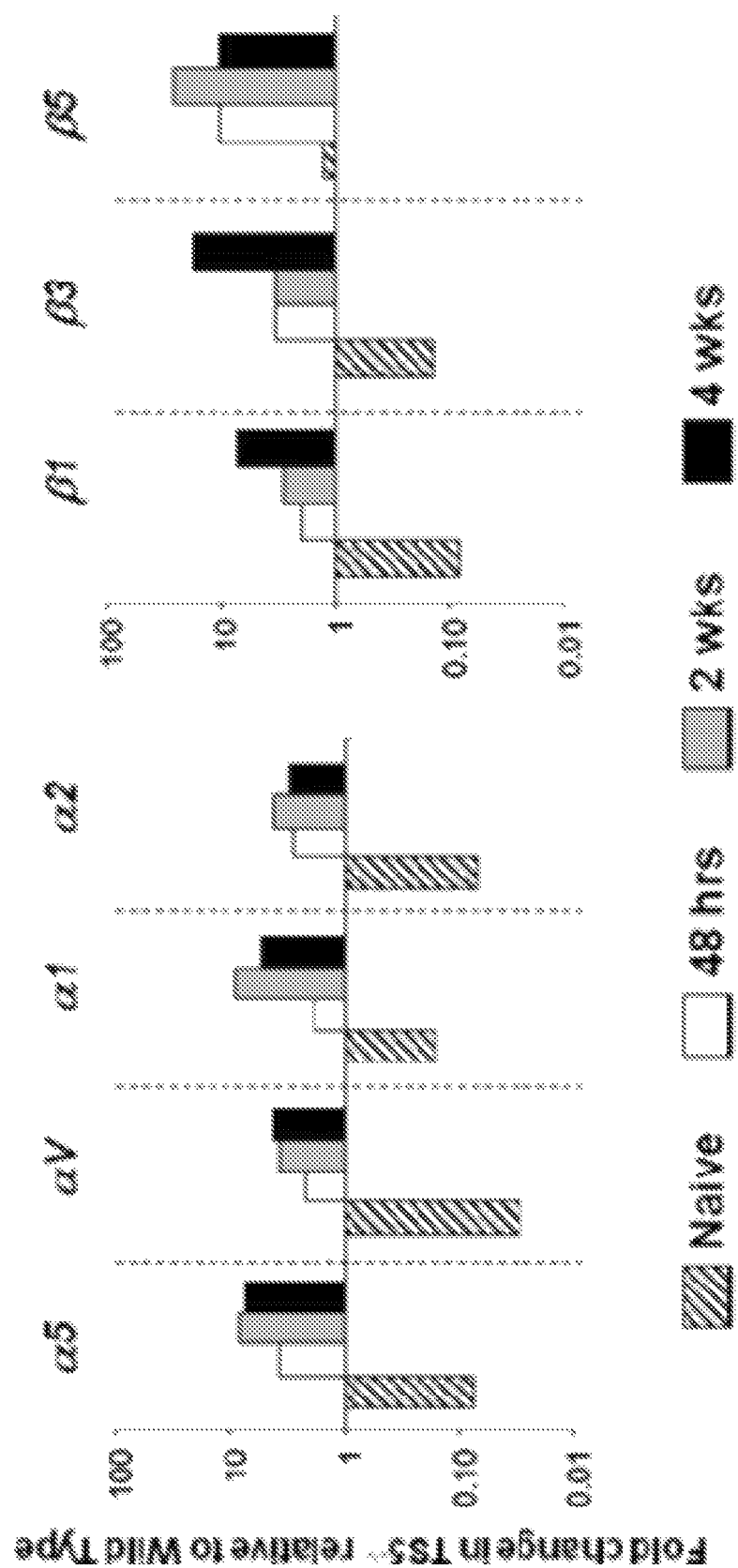
FIG. 9 illustrates the effect of TGF-$\beta$1 injection and treadmill on fold activation of integrin gene expression in Achilles from WT relative to TS5$^{-/-}$ mice. Data for each experimental group were obtained from a pool of 20 tendons. As described in the legend to FIG. 8, values above and below unity indicate a higher and lower activation in the TS5$^{-/-}$ mice relative to WT, respectively.

The Non-Reparative Phenotype of TS5$^{-/-}$ Mice is Accompanied by an Abnormally Elevated Expression of Integrins Since the lack of repair in TS5$^{-/-}$ tendons was accompanied by abnormally low levels of expression of Col1a1 and Col3a1, we next examined the expression of integrins which promote cell binding to collagens (integrins a1, a2, and β1), fibronectin (α5, αV, β1, β3, β5), and laminin (β1). (Luu et al. 2013) The expression level (ΔCT) of integrin genes in naive WT tendons was in the order β1>αV>α5>α1>α2>β3>β5, which was similar to naive TS5$^{-/-}$ (β1>αV>α1>β5>α5>α2>β3) (Table 5). However, the expression of all integrins, except β5, was about 10-fold reduced in naive TS5$^{-/-}$ relative to WT mice, which is consistent with the notion that TS5 is required for cell-matrix interactions involved in fibrogenic wound healing. (Velasco et al. 2011.) The relative fold change in transcript abundance (TS5$^{-/-}$ relative to WT) for each integrin gene (FIG. 9) was determined from the data in Table 5 (as described above for FIG. 8). All integrins showed a similar positive relative fold-change, which despite the lower naive values in TS5$^{-/-}$ resulted in a markedly higher absolute transcript abundance for all integrins in the TS5$^{-/-}$ tendons, at both 2 and 4 weeks. The greater responsiveness of TS5$^{-/-}$ tendons to stimulation of integrin expression by TGF-β1 (Scaffidi et al. 2004) is consistent with the presence of an altered TGF-b1-signaling pathway in dermal fibroblasts from TS5$^{-/-}$ relative to WT mice. (Velasco et al. 2011, Plaas et al, 2011)

Immunohistochemistry of Tendons from TS5$^{-/-}$ Mice Illustrates the Association of Fibrocartilage Formation with Poor Repair The most marked histologic difference between normal and tendinopathic tissue was in the morphology and pericellular matrix of the tendon cells. When Achilles tendons from naive TS5$^{-/-}$ mice were stained for aggrecan or collagen type II, some cells were arranged in linear rows along the collagen fibers, much as seen for naive WTs. However, as previously noted with naive TS5$^{-/-}$ FDL tendons (Wang et al. 2012), some cells also had a rounded morphology and appeared to reside within a disorganized collagen matrix. In contrast to WT mice, in the TS5$^{-/-}$ Achilles tendons a large number of cells with the rounded morphology persisted even at 4 weeks post-injection and treadmill exercise, and all cells stained intensely for aggrecan and collagen type II. Whereas aggrecan was restricted to the immediate pericellular space, col II staining was seen both with cells and diffusely within the fibrillar matrix. The increased staining for these chondrocytic matrix molecules was consistent with the early activation of Acan and Col2a1 gene expression (FIG. 8). In addition, similar to our prior work on WT mice (Bell et al., 2013a), TS5$^{-/-}$ mice showed a persistent increase in cell density in response to TGF-β1 injection (Bell et al., 2013b).

Integrin staining (not shown) and gene expression changes (FIG. 8) provided strong evidence for a change to a fibrochondrocyte phenotype (expressing aggrecan and collagen II) in tendinopathic TS5$^{-/-}$ mice. This change was particularly well illustrated on staining for integrin αV and β3 for the affected cells, as these showed a similar staining pattern as seen in native fibrocartilage in the Achilles tendon-bone insertion site (not shown). Non-immune controls were essentially negative for both antibodies.

Figure 10:
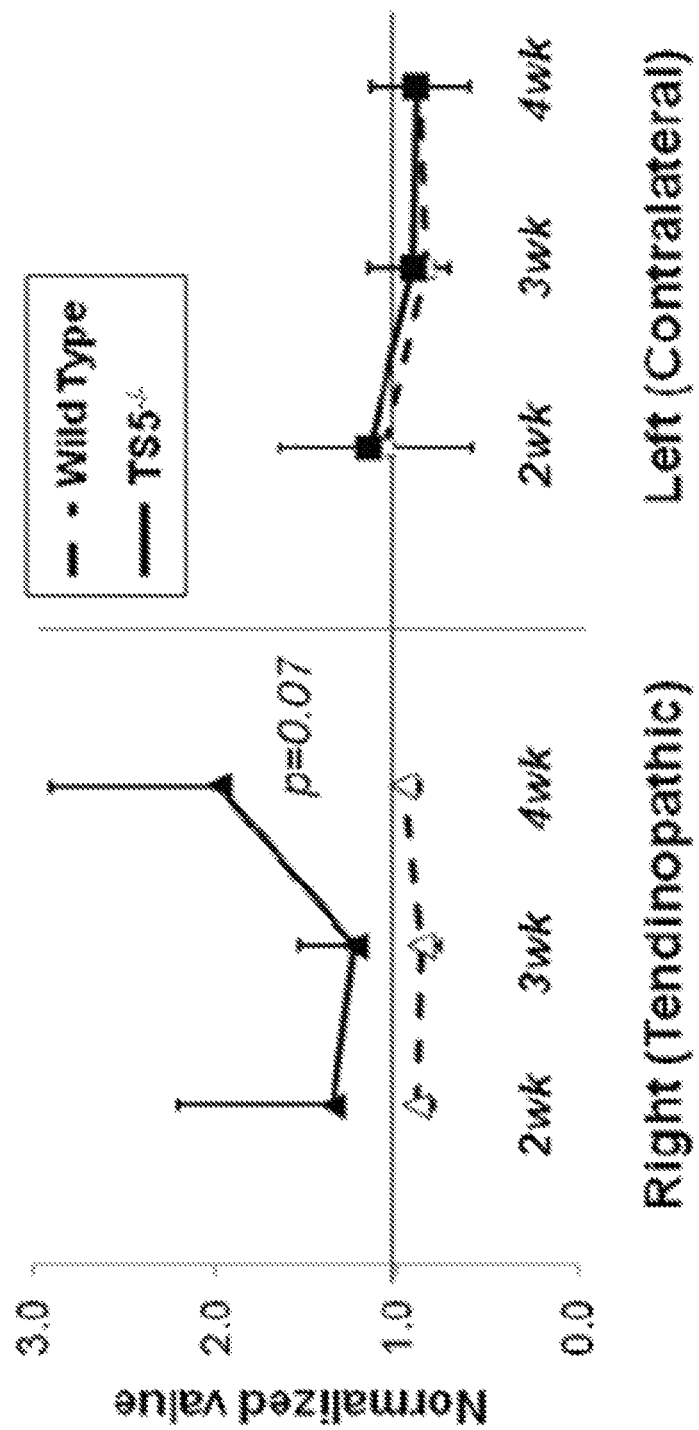
FIG. 10. Gait analysis on TreadScan illustrates the effect of TGF-$\beta$1 injection and treadmill exercise on swing time of WT (n=4) and TS5$^{-/-}$ (n=5) mice. Gait parameters of each mouse were normalized to their baseline (pre-injection)

TGF-β1 injection with treadmill exercise in WT mice resulted in no effects on gait parameters in the affected limb and a small reduction in pawprint area (p=0.058, right vs. left, ANOVA) at 4 weeks. By comparison, for TS5$^{-/-}$ mice at 4 weeks, in addition to a minor reduction in pawprint area, swing time of the injected limb increased (p=0.07, FIG. 10). Neither genotype exhibited alterations in the swing time of the contralateral limb. Of note, the pawprint area, indicative of limb loading, was the same for both healed and nonhealed Achilles tendons, indicating that this parameter may not be a reliable outcome measure for healing efficacy in our model.

Staining for aggrecan and hyaluronan in skin of TS5$^{-/-}$ mice 15 days post wounding showed co-localization of aggrecan and hyaluronan as shown in FIG. 11. Staining for aggrecan and hyaluronan was intracellular or pericellular.

We have previously shown in WT mice that tendinopathy generated by TGF-β1 injection can be healed by treadmill exercise, wherein tendon tensile properties were restored to those of uninjured mice, demonstrating a therapeutic role of biomechanical stimulation (Bell et al., 2013a). However, when the same model was applied to TS5$^{-/-}$ mice (Bell et al., 2013b), mechanical loading was ineffective in healing the tendinopathy. Moreover, the persistently impaired mechanical properties of TS5$^{-/-}$ tendons (FIG. 7) was accompanied by an abundance of chondrocytic shaped, aggrecan/collagen II-enriched cells (not shown) and markedly decreased fibrogenic gene expression relative to WT tendons (FIG. 8). These differences are consistent with an inappropriate chondrogenic response in TS5$^{-/-}$ mice during healing of fibrous connective tissue. (Velasco et al. 2011, Bell et al. 2013a, de Vlaming et al. 2012) Either removal of TS5 by genetic ablation (Bell et al., 2013b) or replacement of treadmill exercise with cage-only activity (Bell et al. 2013a) were found to prevent the repair process. Hence, collectively these results indicate that healing of tendinopathy in our murine model requires both mechanical loading and TS5.

Moreover, the results strengthen the concept that recovery of biomechanical properties in this model requires the removal of aggrecan-rich deposits (ARDS) from the tendon body (Wang et al. 2012, Bell et al. 2013a) Since human tendinopathies are commonly accompanied by chondroid regions of tendon matrix, it becomes important to determine whether such deposits are a by-product of, or a major pathogenic factor in, the human disease (Corps et al, 2006, Corps et al. 2012, Samiric et al., 2009). As we have shown (Bell et al., 2013a, 2013b), the persistence of an aggrecan-rich pericellular matrix can lead to the development of fibrocartilaginous regions and associated disruption of collagen fiber organization, within the body of the tendon. These changes may result in impaired tensile properties (FIG. 7) of such tissue regions. This is also consistent with the change in gait which might result from the loss of tendon tensile properties per se, or from adaptive gait changes secondary to those of the tendon. In addition, in a series of human Achilles samples, quantitative analysis of aggrecan IHC and histopathological scoring exhibited a strong positive correlation consistent with a causative relationship between aggrecan accumulation and tendinopathy. (Burssens et al., 2013)

In summary, our studies suggest that stimulating the pathway which facilitates removal of aggrecan from tendon progenitor cells, and also eliminates ARDs from the tissue, should be effective in promoting the healing of those tendinopathies which involve excessive mucoid deposition. Since it appears that elimination of ARDs can be induced by controlled mechanical loading in mice and humans, we propose that appropriate exercise, together with local delivery of chondrolytic biologics may markedly improve therapeutic outcomes for patients with tendinopathies in which cartilage-like matrix deposits are present in the body of the tendon.

Epigenetic Changes in a Murine Model of Tendinopathy
Methods:

Animals: 12-wk C57BL/6 WT mice underwent two injections (2 days apart) in which 6 ul of 100 ng rhTGF-b1 was injected directly into Achilles tendon (bilaterally for acute time points, and unilaterally for chronic time points). Mice were allowed normal cage activity for 3 days (acute) or 14 days (chronic/repair) [5]. Injected groups were compared to naïve (uninjured) mice. Gene Analysis: 12-20 tendons from each experimental group were combined for RNA preparation (Naïve: 2 pools, acute: 3 pools, chronic/repair: 2 pools). Individual QPCR assays were performed using inventoried primers [Velasco et al., 2011] from Thermo-Lifetech. ΔCt (Ct for gene of interest minus Ct for Gapdh) for each gene and pooled sample was determined in triplicate. Fold change was calculated as $2^{-\Delta\Delta Ct}$ relative to naive levels. The same RNA preparations were used on the array plates (PAMM-085Z, Qiagen). Briefly, cDNA synthesis was performed with 0.5 ug of mRNA using the Qiagen's RT$^2$ first strand kit. The cDNA was then incorporated into the QPCR array which utilizes SYBR. The 84 genes of the array involved in chromatin modification are separated into 8 groups based on function. Statistics and Pathway Analysis: The ΔCt's for each experimental group were compared using a 1-way ANOVA followed by Tukey's post-hoc tests (p<0.05). The Tukey's p-values for each comparison were imported into MetaCore software (Thomson Reuters) to identify pathways of interest based on statistically significant differences between groups.

Results:

Individual QPCR assays of matrix protein expression replicated our earlier findings [Bell et al. J Biomech, 2013], which included an increase of Col3a1, Acan, and Mmp3 expression at 3 days post-injury and further increases at 14 days [FIG. 12A]. The expression of Col1a1, Col1a2 and Col2a1 was not altered at 3 days but activation of Col1a1 and Col2a1 was seen at 14 days. Array analysis showed that the 3 day response was accompanied by a marked up-regulation of Pak1, Aurkb, Aurka, and Esco2, which are genes characteristic of cell proliferation and phenotypic change. At 3 days, 52% of chromatin modification enzyme genes were down-regulation (>2 fold) with 42% of genes remaining unaffected. At 14 days post-injury, 96% of genes were <2 fold up or down-regulated, suggesting an overall normalization to naïve levels. Aurkb and Kdm5c were the only genes up-regulated at 14 days (>2-fold). MetaCore pathway analysis suggested an important role of four genes in development of this injury model: Egr1, Ep300, Pak1, and Rps6ka3. At both 3 and 14 days post-injury, Egr1 expression was down-regulated (4.5 fold) and there was a transient increase in Pak1 (3 fold) and decrease in Rps6ka3 (6 fold) at 3 days [FIG. 12B]. Moreover, Ep300 expression was unaffected at 3 days but became activated at 14 days (3 fold). Table 6 describes diseases associated with altered expression of these genes (anoxia, fibrosis, etc.) as well as the role of their translated proteins in the regulation of other genes and proteins studied in tendon pathology. Most notably, three genes (Hdac9, Ncoa1, and Ncoa3), whose protein products interact with the products of Egr1, Ep300, Pak1, and/or Rps6ka3, all exhibited marked down-regulation (~4 fold), but at 3 days only [FIG. 12C]. Genes pinpointed here are involved in pathways related to cell proliferation/apoptosis (Egr1, Ep300, Rps6ka3, Pak1), cytoskeletal remodeling (Egr1, Rps6ka3), differentiation (Rps6ka3, Pak1), epithelial-to-mesenchymal transition (Egr1, Pak1), TGFb signaling (Ep300, Rps6ka3), and cell adhesion (Pak1). This appears reasonable, since the cellular responses to injury in this model most likely involve progenitor cell proliferation and differentiation, along with interactions of the cells with the complex matrix of tendon collagens and proteoglycans.

CONCLUSIONS

A previously established TGFb injury model in murine Achilles tendons [Bell et al., J Biomech 2013] was expanded upon to study the mechanisms of epigenetic regulation in tendon repair directed towards identifying targets for therapeutic intervention with biologics. A characteristic acute response was observed at 3 days by the increase in cell proliferation genes such as Pak1, Aurkb, Aurka, and Esco2, which was associated with a marked down-regulation of many of the genes involved in chromatin remodeling. At 14 days most of the affected genes had returned to normal levels, consistent with a reparative phase. Kdm5c (lysine specific demethylase for histone H3K4) was one of the only genes that remained up-regulated at 14 days. Ep300, one of the genes identified by MetaCore, is also an H3K4 demethylase, suggesting that modification of H3K4 may control tendon repair. This role for H3K4 may be related to the finding that hypoxia (an environmental stressor often invoked as tendinopathic [Millar et al., Ann Rheum Dis 2012]) blocks H3K4 methylation in many cancer cell lines. Another gene of interest, Egr1, has been identified previously as a key factor in tendon development [Lejard et al. J Boil Chem 2010, Liu et al. Cell and Tissue Res, 2014]. Expression levels of this gene were low at both 3 and 14 days post-injury which may affect production of collagen types I and II during tendon healing. Further, the protein products of Egr1 and Pak1 are involved in transcriptional regulation of histone deacetylases such as HDAC3 and HDAC9. This could be relevant because HDAC inhibitors have been found therapeutically useful in conditions such as cancer and immunological disorders where hypoxia [Chen et al. J Biomed Biotech 2011] and inflammation [Grabiec et al. Crit Rev Immunol, 2011] have been implicated. When taken together, modulators of H3K4 methylation and/or specific HDAC inhibitors may represent therapeutic approaches to human tendinopathies.

Hypoxia in Tendonopathy

METHODS Under IACUC approval, 12-wk C57BL/6 WT and TS5KO male mice received two 6-μL injections, 2 days apart, of 100 ng rhTGF-β1 into the Achilles tendon. Mice were allowed normal cage activity for 3 or 14 days. Injected groups were compared to a control group of naïve mice. 12-20 tendons from each experimental group were combined for RNA preparation using 2-3 pools per experimental group. QPCR for individual matrix-protein genes was performed in triplicate, on cDNA synthesized with the SuperScript™ First Strand (Invitrogen) system from 0.5 μg of RNA, using inventoried Taqman® (Life Technologies) primer-probe sets [Bell et al. J Biomech, 2013]. For hypoxia gene expression arrays (PAMM-032ZA, Qiagen), cDNA synthesis was performed using the $RT^2$ First Strand (Qiagen) kit with 0.5 μg of mRNA from the same RNA preparations. For analysis, ΔCt (Ct for gene of interest minus Ct for B2m) was used to calculate abundance $2^{-(\Delta Ct)} \ast 1000$ and fold change, $2^{(-\Delta\Delta Ct)}$, relative to naïve levels for each genotype.

RESULTS Overall, TS5KO mice exhibited a higher percentage of up-regulated hypoxia genes (>2-fold) at both 3 and 14 days post-injury (44% and 56%, respectively) compared to WT mice (38% and 5%, respectively). Naïve TS5KO mice (relative to WT) also had a marked (>2-fold) down-regulation of 87% of genes related to hypoxia. The 3-day post-injury response in WT mice was accompanied by up-regulation (2.3-fold) in hypoxia inducible factor 1a (Hif1a), a master regulator of the cellular homeostatic response to hypoxia [Semenza, Ann Rev Cell Dev Bio, 1999]. Hif1a expression returned to naïve levels (1.1-fold) at 14 days. Conversely, in TS5KO mice, Hif1a was up-regulated at both 3 and 14 days post-injury (5-fold and 3.9-fold, respectively). The functional gene groups most affected by injury included genes involved in metabolism and angiogenesis, most notably Pkm and Angptl4, respectively. At 3 days post-injury, these genes were up-regulated (>2 fold) in both WT and TS5KO mice. However at 14 days, expression returned to naïve levels in WT mice but remained up-regulated in TS5KO mice. Expression of Hif1a was found to be highly correlated to the expression of aggrecan (Acan) in both genotypes over the injury time period (FIG. 13), while Pkm and Angptl4 were both highly correlated with Acan expression in TS5KO ($R^2$=0.91 and 0.83, respectively) but not WT mice ($R^2$=0.11 for both).

DISCUSSION The present study implicates hypoxia in an Achilles tendinopathy model, with both WT and TS5KO mice exhibiting an up-regulation in ~40% of hypoxia responsive genes at 3 days post-injury. However at 14 days, >50% of hypoxia genes remain up-regulated in TS5KO, but not WT mice, possibly contributing to its more severe tendinopathic phenotype [Bell et al., JOR 2013]. Given the pathogenic accumulation of aggrecan in diseased tendon, the high correlation between the expression of Hif1a and Acan in both genotypes further supports the notion that hypoxia may play a role in the development of tendinopathy. Pkm and Angptl4 are both highly correlated to Acan expression in TS5KO but not WT mice, suggesting that the presence of the ADAMTS5 protein may contribute to tendon healing via regulation of the expression of these genes. This study has demonstrated that hypoxia-related pathways regulated by ADAMTS5 may be viable clinical targets in treating tendinopathy. Mechanical stimulation via treadmill running will increase oxygen diffusion throughout the tissue and regulate angiogenic factors, such as Angptl4, to promote tendon healing [Mousavizadeh et al., PLos One, 2014].

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

LITERATURE CITED

Arya, S., Kulig, K., 2010. Tendinopathy alters mechanical and material properties of the Achilles tendon. Journal of Applied Physiology 108, 670-675.

Bell R, Li J, Gorski D J, et al. 2013a. Controlled treadmill exercise eliminates chondroid deposits and restores tensile properties in a new murine tendinopathy model. J Biomech 46: 498-505.

Bell R, Li J, Shewman E F, et al. 2013b. ADAMTS5 is required for biomechanically-stimulated healing of murine tendinopathy. J Orthop Res 31:1540-8.

Burssens A, Forsyth R, Bongaerts W, et al. 2013. Arguments for an increasing differentiation towards fibrocartilaginous components in midportion Achilles tendinopathy. Knee Surg Sports Traumatol Arthrosc 21:1459-67.

Chang, J., Thunder, R., Most, D., Longaker, M. T., Lineaweaver, W. C., 2000. Studies in flexor tendon wound healing: neutralizing antibody to TGF-beta1 increases postoperative range of motion. Plastic and Reconstructive Surgery 105, 148-155.

Chen et al., J Biomed Biotech, 2011

Corps, A. N., Robinson, A. H., Movin, T., Costa, M. L., Hazleman, B. L.,

Riley, G. P., 2006. Increased expression of aggrecan and biglycan mRNA in Achilles tendinopathy. Rheumatology 45, 291-294.

Corps, A. N., Robinson, A. H., Harrall, R. L., Avery, N. C., Curry, V. A., Hazleman, B. L., Riley, G. P., 2012. Changes in matrix protein biochemistry and the expression of mRNA encoding matrix proteins and metalloproteinases in posterior tibialis tendinopathy. Annals of the Rheumatic Diseases 71, 746-752.

de Mos, M., Koevoet, W., van Schie, H. T., Kops, N., Jahr, H., Verhaar, J. A., van Osch, G. J., 2009. In vitro model to study chondrogenic differentiation in tendinopathy. The American Journal of Sports Medicine 37, 1214-1222.

de Vlaming A, Sauls K, Hajdu Z, et al. 2012. Atrioventricular valve development: New perspectives on an old theme. Differentiation 84: 103-116.

Estellar, N Engl J Med, 2008.

Grabiec et a., Crit Rev Immunol, 2011.

Kannus et al., J Bone Joint Surg Am, 1991.

Lejard et al., J Biol Chem, 2010.

Li J, Anemaet W, Diaz M A, et al. 2011. Knockout of ADAMTS5 does not eliminate cartilage aggrecanase activity but abrogates joint fibrosis and promotes cartilage aggrecan deposition in murine osteoarthritis models. J Orthop Res 29: 516-522.

Li, J., Gorski, D. J., Anemaet, W., Velasco, J., Takeuchi, J., Sandy, J. D., Plaas, A., 2012. Hyaluronan injection in murine osteoarthritis prevents TGFbeta 1-induced synovial neovascularization and fibrosis and maintains articular cartilage integrity by a CD44-dependent mechanism. Arthritis Research & Therapy 14, R151.

Liu et al., Cell and Tissue Res, 2014.

Luu N T, Glen K E, Egginton S, Rainger G E, Nash G B. 2013. Integrin-substrate interactions underlying shear-induced inhibition of the inflammatory response of endothelial cells. Thromb Haemost 109: 298-308.

Malfait A M, Ritchie J, Gil A S, et al. 2010. ADAMTS-5 deficient mice do not develop mechanical allodynia associated with osteoarthritis following medial meniscal destabilization. Osteoarthritis Cartilage 18: 572-580.

Maeda, T., Sakabe, T., Sunaga, A., Sakai, K., Rivera, A. L., Keene, D. R., Sasaki, T., Stavnezer, E., Iannotti, J., Schweitzer, R., Ilic, D., Baskaran, H., Sakai, T., 2011. Conversion of mechanical force into TGF-beta-mediated biochemical signals. Current Biology 21, 933-941.

Millar et al., Ann Rheum Dis, 2012.

Mousavizadeh et al., PLoS One, 2014.

Pingel J, Fredberg U, Qvortrup K, Larsen J O, Schjerling P, Heinemeier K, Kjaer M and Langberg H, 2012. Local biochemical and morphological differences in human Achilles tendinopathy: a case control study. BMC Musculoskeletal Disorders 13, 53.

Plaas, A., Osborn, B., Yoshihara, Y., Bai, Y., Bloom, T., Nelson, F., Mikecz, K., Sandy, J. D., 2007. Aggrecanolysis in human osteoarthritis: confocal localization and biochemical characterization of ADAMTS5-hyaluronan complexes in articular cartilages. Osteoarthritis and Cartilage 15, 719-734.

Plaas, A., Li, J., Riesco, J., Das, R., Sandy, J. D., Harrison, A., 2011. Intraarticular injection of hyaluronan prevents cartilage erosion, periarticular fibrosis and mechanical allodynia and normalizes stance time in murine knee osteoarthritis. Arthritis Research & Therapy 13, R46.

Plaas A, Velasco J, Gorski D J, et al. 2011. The relationship between fibrogenic TGFbeta1 signaling in the joint and cartilage degradation in post-injury osteoarthritis. Osteoarthritis Cartilage 19: 1081-1090.

Plaas, A., Sandy, J. D., Liu, H., Diaz, M. A., Schenkman, D., Magnus, R. P., Bolam-Bretl, C., Kopesky, P. W., Wang, V. M., Galante, J. O., 2011. Biochemical identification and immunolocalizaton of aggrecan, ADAMTS5 and inter-alpha-trypsin-inhibitor in equine degenerative suspensory ligament desmitis. Journal of Orthopaedic Research 29, 900-906.

Robinson et al., Epi, 2012.

Samiric, T., Parkinson, J., Ilic, M. Z., Cook, J., Feller, J. A., Handley, C. J., 2009. Changes in the composition of the extracellular matrix in patellar tendinopathy. Matrix Biology 28, 230-236.

Scaffidi A K, Petrovic N, Moodley Y P, et al. 2004. Alpha (v)beta(3) integrin interacts with the transforming growth factor beta (TGFbeta) type II receptor to potentiate the proliferative effects of TGFbeta1 in living human lung fibroblasts. J Biol Chem 279: 37726-37733.

Semenza, Ann Rev Cell Dev Bio, 1999.

Shoshani et al., Stem Cells, 2014.

Silbernagel, K. G., Brorsson, A., Lundberg, M., 2011. The majority of patients with Achilles tendinopathy recover fully when treated with exercise alone: a 5-year follow-up. The American Journal of Sports Medicine 39, 607-613.

Velasco, J., Li, J., DiPietro, L., Stepp, M. A., Sandy, J. D., Plaas, A., 2011. Adamts5 deletion blocks murine dermal repair through CD44-mediated aggrecan accumulation and modulation of transforming growth factor beta1 (TGFbeta1) signaling. The Journal of Biological Chemistry 286, 26016-26027.

Wang, V. M., Banack, T. M., Tsai, C. W., Flatow, E. L., Jepsen, K. J., 2006. Variability in tendon and knee joint biomechanics among inbred mouse strains. Journal of Orthopaedic Research 24, 1200-1207.

Wang, V. M., Bell, R. M., Thakore, R., Eyre, D. R., Galante, J. O., Li, J., Sandy, J. D., Plaas, A., 2012. Murine tendon function is adversely affected by aggrecan accumulation due to the knockout of ADAMTS5. Journal of Orthopaedic Research 30, 620-626.

TABLE 1

Effect of TGF-$\beta1$ injection and cage activity on biomechanical properties of the Achilles tendon

| TREATMENT | CSA (mm$^2$) | Stress Relaxation (%) | Maximum Load (N) | Stiffness (N/mm) | Maximum Stress (MPa) | Tensile Modulus (MPa) |
|---|---|---|---|---|---|---|
| Acute/Naïve | 1.42 | 1.12 | 0.62 | 0.57 * | 0.46 * | 0.44 * |
| p-value | 0.242 | 0.34 | 0.09 | 0.033 | 0.002 | <0.001 |
| 2 wks/Naïve | 1.86 * | 1.16 | 0.66 | 0.57 * | 0.34 * | 0.28 * |
| p-value | 0.003 | 0.31 | 0.19 | 0.034 | <0.001 | <0.001 |
| 4 wks/Naïve | 1.47 | 1.29 | 0.62 | 0.58 * | 0.39 * | 0.40 * |
| p-value | 0.160 | 0.07 | 0.09 | 0.040 | <0.001 | <0.001 |

CSA: cross-sectional area

For each parameter, ratio of mean values of experimental to naive group is provided.

* Indicates statistically significant alterations relative to naïve tendons.

TABLE 2

Effect of TGF-$\beta1$ injection and cage activity on gene expression

| TREATMENT | Col1a1 ΔCT | Col2a1 ΔCT | Col3a1 ΔCT | Fn1 ΔCT | Acan ΔCT | Adamts5 ΔCT | Mmp3 ΔCT |
|---|---|---|---|---|---|---|---|
| Naïve | −0.14 (0.16) | 16.65 (0.39) | 4.04 (0.07) | 1.38 (0.03) | 15.91 (0.61) | 7.26 (0.07) | 11.35 (0.20) |
| Acute | −1.61 (0.38) | 16.95 (0.64) | 2.08 (0.19) | 0.35 (0.11) | 10.56 (0.08) | 8.44 (0.14) | 6.58 (0.14) |
| $^1$p | 0.015 | 0.625 | 0.037 | 0.0026 | 0.0036 | 0.027 | 0.0003 |
| 2 weeks | −5.13 (0.11) | 12.28 (0.15) | −0.32 (0.42) | −0.43 (0.43) | 7.92 (0.37) | 7.27 (0.16) | 4.70 (0.31) |
| $^1$p | <0.00001 | 0.0009 | 0.0028 | 0.0183 | 0.0004 | 0.9445 | <0.00001 |
| 4 weeks | −3.52 (0.51) | 10.90 (0.38) | 3.99 (0.16) | 0.36 (0.16) | 9.78 (0.45) | 7.83 (0.03) | 4.50 (0.31) |
| $^1$p | 0.022 | <0.00001 | 0.215 | 0.0066 | 0.00025 | 0.0014 | <0.00001 |

Data presented are mean values, with standard deviation in parentheses $^1$p values represent comparisons to ΔCT of Naïve samples

TABLE 3

Effect of treadmill running on biomechanical properties of Achilles tendons from tendinopathy model

| TREATMENT | CSA | Stress Relaxation | Maximum Load | Stiffness | Maximum Stress | Tensile Modulus |
|---|---|---|---|---|---|---|
| 2 wks TM/Cage | 0.80 | 1.01 | 0.69 | 0.94 | 0.81 | 1.25 |
| p | (0.16) | (0.93) | (0.28) | (0.81) | (0.38) | (0.19) |
| 4 wks TM/Cage | 0.88 | 0.82 | 2.05* | 1.65* | 2.41* | 1.83* |
| p | (0.37) | (0.09) | (0.02) | (0.04) | (0.001) | (0.02) | from post hoc analyses relative to Cage value = 1;

*Indicates statistically significant alterations relative to Naïve values.

TABLE 4

Effect of TGF-β1 injection and TM exercise on matrix gene expression in Achilles tendons of WT and TS5$^{-/-}$ mice

| | Col1a1 | | Col2a1 | | Col3a1 | |
|---|---|---|---|---|---|---|
| | WT[a] | TS5$^{-/-}$ | WT[a] | TS5$^{-/-}$ | WT[a] | TS5$^{-/-}$ |
| Naïve | −0.14 (0.16) | 1.86 (0.60) | 16.65 (0.64) | 10.93 (0.75) | 4.04 (0.07) | 8.27 (0.32) |
| Acute | −1.61 (0.38) | −1.93 (0.06) | 16.95 (0.64) | 15.69 (0.23) | 2.08 (0.19) | 1.28 (0.21) |
| [1]p | 0.015 | 0.0001 | 0.625 | <0.00001 | 0.037 | <0.00001 |
| 2 wks | −4.47 (0.10) | −4.32 (0.32) | 9.96 (0.02) | 12.72 (0.36) | 0.94 (0.08) | 6.00 (0.13) |
| [1]p | <0.00001 | <0.00001 | 0.001 | 0.003 | <0.00001 | <0.00001 |
| 4 wks | −0.11 (0.15) | −0.44 (0.19) | 15.66 (0.18) | ND | 8.96 (0.04) | 16.08 (0.73) |
| [1]p | 0.290 | 0.002 | 0.034 | | <0.00001 | <0.00001 |

| | Fn1 | | Acan | |
|---|---|---|---|---|
| | WT[a] | TS5$^{-/-}$ | WT[a] | TS5$^{-/-}$ |
| Naïve | 1.38 (0.03) | 1.13 (0.57) | 15.91 (0.61) | 13.79 (0.49) |
| Acute | 0.35 (0.11) | −0.23 (0.15) | 10.56 (0.08) | 8.14 (0.84) |
| [1]p | 0.003 | 0.047 | 0.004 | 0.002 |
| 2 wks | −3.19 (0.23) | −3.67 (0.33) | 7.33 (0.29) | 8.76 (0.36) |
| [1]p | 0.001 | 0.001 | 0.001 | <0.00001 |
| 4 wks | −1.04 (0.47) | 1.56 (0.15) | 13.44 (0.42) | 11.44 (0.66) |
| [1]p | 0.012 | 0.319 | 0.011 | 0.019 |

Data presented are mean ΔCt values, with standard deviation in parentheses
[1]p values represent comparisons to ΔCT of naïve samples within each genotype
[a]WT data are from Bell et al. (2013a)

TABLE 5

Effect of TGF-β1 injection and TM exercise on integrin gene expression in Achilles tendons of WT and TS5$^{-/-}$ mice.

| Group | Genotype | Beta1 | Beta3 | Beta5 | Alpha5 | AlphaV | Alpha1 | Alpha2 |
|---|---|---|---|---|---|---|---|---|
| Naïve | WT | 1.69 (0.15) | 11.17 (0.21) | 11.47 (0.13) | 7.44 (0.14) | 5.28 (0.15) | 8.42 (0.15) | 9.48 (0.08) |
| | TS5$^{-/-}$ | 5.30 (0.06) | 14.02 (0.23) | 11.13 (0.18) | 11.16 (0.33) | 10.36 (0.20) | 11.02 (0.13) | 13.31 (0.45) |
| Acute | WT | 3.25 (0.04) | 10.90 (0.57) | 12.73 (0.67) | 6.19 (0.06) | 6.62 (0.19) | 8.75 (0.12) | 12.33 (0.26) |
| | p | 0.002 | 0.622 | 0.078 | 0.001 | <0.001 | 0.041 | 0.001 |
| | TS5$^{-/-}$ | 2.20 (0.30) | 9.17 (0.21) | 9.37 (0.30) | 4.29 (0.43) | 5.40 (0.15) | 7.86 (0.05) | 10.81 (0.42) |
| | p | 0.002 | <0.001 | 0.039 | 0.004 | <0.00001 | <0.001 | 0.002 |
| 2 wks | WT | 1.19 (0.28) | 8.90 (0.17) | 10.40 (0.56) | 6.50 (0.13) | 5.27 (0.26) | 8.75 (0.23) | 9.68 (0.27) |
| | p | 0.070 | <0.001 | 0.073 | 0.011 | 0.961 | 0.115 | 0.325 |
| | TS5$^{-/-}$ | −0.36 (0.27) | 7.18 (0.29) | 5.66 (0.50) | 3.43 (0.37) | 3.34 (0.02) | 5.61 (0.17) | 7.61 (0.29) |
| | p | <0.001 | <0.00001 | 0.001 | <0.00001 | <0.00001 | <0.00001 | <0.001 |
| 4 wks | WT | 2.58 (0.08) | 12.06 (0.17) | 9.52 (0.41) | 8.76 (0.06) | 6.34 (0.69) | 8.87 (0.12) | 10.43 (0.24) |
| | p | 0.00294 | 0.131 | 0.07743 | <0.001 | 0.111 | 0.016 | 0.013 |
| | TS5$^{-/-}$ | −0.25 (0.04) | 7.90 (0.05) | 6.17 (0.17) | 5.85 (0.09) | 4.29 (0.39) | 6.41 (0.20) | 8.82 (0.13) |
| | p | <0.00001 | <0.001 | <0.00001 | <0.001 | <0.001 | <0.00001 | 0.002 |

Data presented are mean ΔCt values, with standard deviation in parentheses;
p values represent comparisons to ΔCT of naïve samples within each genotype

TABLE 6

Primary candidate genes following MetaCore pathway analysis: Listing for each gene includes associated diseases and protein product interactions which are characterized as outgoing (regulation on other proteins) or incoming (listed protein has an effect on the candidate protein product). These interactions are further broken down into activation/inhibition and type of modification.

| | | Interactions | |
|---|---|---|---|
| Gene | Associated Diseases | Outgoing | Incoming |
| Egr1 | Anoxia Arthritis Fibrosis Wounds and Injuries | Activation Transcriptional Regulation: Col1a1, Col1a2, Egr1, Sox9, TGFb1/2, Ep300, PDGF A/B/C Influence on Expression: Scleraxis Unspecified Binding: Histone H4, Smad3 Transcriptional Regulation: BMP 2/4/6/7, Col2, Dnmt3b, Has3, | Activation Transcriptional Regulation: Egr1, p53, Ep300 Influence on Expression: Erk1/2, FGF1/2, PDGFR, PDGFb, TGFb1, Smad3 |

TABLE 6-continued

Primary candidate genes following MetaCore pathway analysis: Listing for each gene includes associated diseases and protein product interactions which are characterized as outgoing (regulation on other proteins) or incoming (listed protein has an effect on the candidate protein product). These interactions are further broken down into activation/inhibition and type of modification.

| | | Interactions | |
|---|---|---|---|
| Gene | Associated Diseases | Outgoing | Incoming |
| Ep300 | Anoxia | Hdac 1/2/9, Prmt8, Smad1, nNOS, TGFb3 Activation Acetylation: NF-κB Binding: Smad1/4 Covalent Modification: Smad2/3 Transcriptional Regulation: BMP2/4/7, CD44, Col1a1, Col2, iNOS, Egr1, Sox9, Mmp13 Unspecified Acetylation: Histone 2A/2B, TGFbRI, PDGFRb, Smad5 Covalent Modification: Histone H2/H3/H4 Transcriptional Regulation: Col1a2, Has1, TGFb1, TGFbRII | Inhibition Transcriptional Regulation: Hdac1/2 Activation Binding: Ncoa2/3, Smad 1/4, Sox9 Transcriptional Regulation: Egr1, Erk1/2 Hdac3/6 Unspecified Binding: Rps6ka3, Ncoa1 |
| Pak1 | Wounds and Injuries | Activation Phosphorylation: Erk3/4 Inhibition Binding: Erk1/2 Unspecified Binding: TGFbR1/II, Smad1/2 Phosphorylation: Histone H1/H3/H4 | Inhibition Binding: Smad4, Hdac2 |
| Rps6ka3 | Inflammation | Activation Transcriptional Regulation: Egr1 Unspecified Binding: Ep300 | Activation Phosphorylation: Erk1/2 |

The invention claimed is:

1. A method of treating a musculoskeletal disorder in a subject; the method comprising administering an enzymatic therapy to reduce an amount of an aggrecan-hyaluronan matrix of the subject from a treatment site in the subject to treat the musculoskeletal disorder and measuring a level of the aggrecan-hyaluronan matrix before administering the enzymatic therapy and after administering the therapy to determine a reduction in the amount of the aggrecan-hyaluronan matrix; and wherein the enzymatic therapy comprises chondrolytic biologics.

2. The method according to claim 1, further comprising administering an exercise therapy to reduce the amount of the aggrecan-hyaluronan matrix.

3. The method according to claim 1, comprising increasing oxygen diffusion to an injured tissue through activity.

4. The method according to claim 1, wherein the treatment site is selected from the group consisting of bone, joint capsule, muscle ligaments and tendons.

5. The method according to claim 1, wherein the musculoskeletal disorder is selected from the group consisting of osteoarthritis, long-bone fracture, tendinopathy, synovitis, myositis and non-healing chemical wounds.

* * * * *